United States Patent
Sugaya et al.

(10) Patent No.: US 7,618,621 B2
(45) Date of Patent: Nov. 17, 2009

(54) MAMMALIAN MULTIPOTENT NEURAL STEM CELLS AND COMPOSITIONS, METHODS OF PREPARATION AND METHODS OF ADMINISTRATION THEREOF

(75) Inventors: Kiminobu Sugaya, Willow Springs, IL (US); Tingyu Qu, Chicago, IL (US); Jose S. Pulido, Brookfield, WI (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 660 days.

(21) Appl. No.: 10/342,616

(22) Filed: Jan. 14, 2003

(65) Prior Publication Data

US 2003/0148513 A1  Aug. 7, 2003

Related U.S. Application Data

(60) Provisional application No. 60/348,473, filed on Jan. 14, 2002, provisional application No. 60/357,783, filed on Feb. 19, 2002, provisional application No. 60/376,257, filed on Apr. 29, 2002, provisional application No. 60/381,138, filed on May 8, 2002, provisional application No. 60/404,361, filed on Aug. 19, 2002, provisional application No. 60/430,381, filed on Dec. 2, 2002.

(51) Int. Cl.
   C12N 5/00   (2006.01)
   C12N 5/02   (2006.01)
   C12N 5/06   (2006.01)
   C12N 5/08   (2006.01)

(52) U.S. Cl. .................. 424/93.1; 435/377; 435/368; 435/372; 435/373; 435/366; 435/325; 424/93.7

(58) Field of Classification Search ............ None
See application file for complete search history.

(56) References Cited

U.S. PATENT DOCUMENTS

| | | |
|---|---|---|
| 4,959,368 A | 9/1990 | Awaya |
| 5,104,650 A | 4/1992 | Ralph et al. |
| 5,411,883 A | 5/1995 | Boss et al. |
| 5,589,376 A | 12/1996 | Anderson et al. |
| 5,750,376 A | 5/1998 | Weiss et al. |
| 5,753,506 A | 5/1998 | Johe |
| 5,766,948 A | 6/1998 | Gage et al. |
| 5,851,932 A | 12/1998 | Weiss et al. |
| 5,925,567 A | 7/1999 | Kraus et al. |
| 5,968,829 A | 10/1999 | Carpenter |
| 5,976,523 A | 11/1999 | Awaya et al. |
| 5,980,885 A | 11/1999 | Weiss et al. |
| 6,013,521 A | 1/2000 | Gage et al. |
| 6,020,197 A | 2/2000 | Gage et al. |
| 6,040,180 A * | 3/2000 | Johe .................. 435/377 |
| 6,090,624 A | 7/2000 | Greenwood et al. |
| 6,117,675 A | 9/2000 | Van der Kooy et al. |
| 6,254,865 B1 | 7/2001 | Freed et al. |
| 6,284,245 B1 | 9/2001 | Edge |
| 6,306,575 B1 | 10/2001 | Thomas et al. |
| 6,368,854 B2 | 4/2002 | Weiss et al. |
| 6,497,872 B1 | 12/2002 | Weiss |
| 6,638,501 B1 | 10/2003 | Bjornson |
| 6,670,397 B1 | 12/2003 | Baranowitz |
| 6,787,355 B1 | 9/2004 | Miller et al. |
| 6,808,702 B2 | 10/2004 | Pasricha |
| 6,824,973 B2 | 11/2004 | Tang |
| 6,833,268 B1 | 12/2004 | Green |
| 2001/0038836 A1 | 11/2001 | During et al. |
| 2002/0142457 A1 | 10/2002 | Umezawa et al. |
| 2002/0146821 A1 | 10/2002 | Sanchez-Ramos et al. |
| 2002/0168350 A1 | 11/2002 | Brazelton et al. |
| 2002/0168765 A1 | 11/2002 | Prockop et al. |
| 2003/0053992 A1 | 3/2003 | Rader |
| 2003/0059868 A1 | 3/2003 | Greenwood et al. |
| 2003/0118566 A1 | 6/2003 | Neuman |
| 2003/0139410 A1 | 7/2003 | Sugaya |
| 2003/0148513 A1 | 8/2003 | Sugaya et al. |
| 2003/0219898 A1 | 11/2003 | Sugaya |
| 2004/0034049 A1 | 2/2004 | Okawa |
| 2004/0103448 A1 | 5/2004 | Bjorklund |
| 2004/0106197 A1 * | 6/2004 | Okano et al. .................. 435/368 |
| 2005/0169897 A1 | 8/2005 | Snyder |
| 2005/0181503 A1 | 8/2005 | Goldman |

FOREIGN PATENT DOCUMENTS

| | | |
|---|---|---|
| EP | 0 192 783 | 9/1986 |
| EP | 0 305 184 | 3/1989 |
| EP | 0 612 746 | 8/1994 |
| EP | 0 648 495 | 4/1995 |
| JP | 64-040483 | 2/1989 |
| JP | 64-079183 | 3/1989 |
| JP | 1-139572 | 6/1989 |
| JP | 7-90002 | 4/1995 |
| JP | 8-502172 | 3/1996 |
| JP | 8-325268 | 12/1996 |

(Continued)

OTHER PUBLICATIONS

Coleman et al., Developmental Biology (1969), 19(6): 527-548 Abstract, Caplus Accession No. 1969:420164.*
Kidson et al., Experimental Cell Research, vol. 188, Issue 1, May 1990, pp. 36-41, Abstract.*
Alvarez-Buylla et al., 1997, *J. Neurobiology* 33: 585-601.
Benninger et al., 2000, *Brain Pathol.* 10: 330-341.
Blakemore et al., 1991, *Trends Neurosci.* 14: 323-327.
Blakemore et al., 2000, *Cell Transplant.* 9: 289-294.
Brannen et al., 2000, *Neuroreport* 11: 1123-8.

(Continued)

Primary Examiner—Daniel C Gamett
(74) Attorney, Agent, or Firm—Timothy H. Van Dyke; Beusse Wolter Sanks Mora & Maire

(57) ABSTRACT

This invention relates to novel mammalian multipotent neural stem cells (MNSCs), compositions thereof, and methods of preparing and administering the cells to diseased, aged or damaged tissue such that the cells properly migrate and differentiate and a neurological or corporal deficit is improved or remedied as a result.

12 Claims, 14 Drawing Sheets

FOREIGN PATENT DOCUMENTS

| | | |
|---|---|---|
| JP | 9-507747 | 8/1997 |
| JP | 9-295946 | 11/1997 |
| JP | 9-328435 | 12/1997 |
| JP | 10-504308 | 4/1998 |
| JP | 2001-504123 | 3/2001 |
| JP | 2001-526884 | 12/2001 |
| JP | 2002-500624 | 1/2002 |
| JP | 2002-502858 | 1/2002 |
| JP | 2002-518990 | 7/2002 |
| WO | WO 87/04928 | 8/1987 |
| WO | WO 89/01938 | 3/1989 |
| WO | WO 93/01275 | 1/1993 |
| WO | WO 94/09119 | 4/1994 |
| WO | WO 94/10292 | 5/1994 |
| WO | WO 94/16718 | 8/1994 |
| WO | WO 95/13364 | 5/1995 |
| WO | WO 96/04789 | 2/1996 |
| WO | WO96/15226 | 5/1996 |
| WO | WO 96/15226 A1 | 5/1996 |
| WO | WO 98/22127 | 5/1998 |
| WO | WO 98/32457 | 7/1998 |
| WO | WO 99/11758 | 3/1999 |
| WO | WO 99/32606 | 7/1999 |
| WO | WO 99/40107 | 8/1999 |
| WO | WO 99/43286 | 9/1999 |
| WO | WO00/29550 | 5/2000 |
| WO | WO 03/60085 A2 | 5/2000 |
| WO | WO 00/69448 | 11/2000 |
| WO | WO 01/11011 | 2/2001 |
| WO | WO 01/34167 | 5/2001 |
| WO | WO 01/53461 A1 | 7/2001 |
| WO | WO 01/59072 | 8/2001 |
| WO | WO 02/064748 | 8/2002 |
| WO | WO03/060085 A2 | 7/2003 |
| WO | WO 03/060085 A2 | 7/2003 |
| WO | 2005/009359 A2 | 2/2005 |

OTHER PUBLICATIONS

Carpenter et al., 1999, *Experimental Neurology* 158: 265-278.
Cattaneo et al., 1996, *Mol. Brain Res*. 42: 161-66.
Doetsch et al., 1999, *Cell* 97: 703-16.
Eckenstein et al., 1994, *Biochem. Pharmacol*. 47: 103-110.
Fricker et al., 1999, *J. Neurosci*. 19: 5990-6005.
Frölichsthal-Schoeller et al., 1999, *NeuroReport* 10: 345-351.
Gonzalez et al., 1995, *Brain Res*. 701: 201-226.
Gould et al., 1999, *Science* 286: 548-552.
Hatton et al., 1992, *Glia* 5: 251-258.
Johansson et al., 1999, *Cell* 96: 25-34.
Kurimoto et al., 2001, Neurosci Let. 306: 57-60.
Lundberg et al., 1996, *Exp. Neurol*. 139: 39-53.
Nishida et al., 2000, Invest Ophthalmol Vis Sci 41: 4268-74.
Pundt et al., 1995, *Brain Res*. 695: 25-36.
Qu et al., 2001, Neuroreport 12: 1127-32.
Rosser et al., 2000, *Eur. J. Neurosci*. 12: 2405-2413.
Rubio et al., 2000, *Mol. Cell. Neurosci*. 16: 1-13.
Svendsen et al., 1998, *J. Neurosci. Methods* 85: 141-152.
Svendsen et al., 1999, *Brain Pathol*. 9: 499-51.
Warfvinge et al., 2001, Exp. Neurol. 169: 1-12.
Williams et al., 1996, *J. Comp. Neurol*. 370: 147-158.
Daadi et al Generation of tyrosine hydroxylase-producing neurons from precursors of the embryonic and adult forebrain. The Journal of Neuroscience. Jun. 1, 1999, vol. 19, No. 11, pp. 4484-4497.
Murphy et al. Neural Stem Cells. Journal of Investigative Dermatology Symposium Proceedings. Aug. 1997, vol. 2, No. 1, pp. 8-13.
Mazurova et al. New therapeutic approaches for the treatment of Huntington's disease. Acta Medica 2001, vol. 44, No. 4 pp. 119-123.
Memberg et al. Proliferation, differentiation and survival of rat sensory neuron precursors in vitro require specific trophic factors. Molecular and Cellular Neuroscience. Aug. 1995, vol. 6, No. 4, pp. 323-335.

Andrews et al. TNFa potentiates IFN g-induced cell death in oligodendrocyte progenitors. Journal of Neuroscience Research. Dec. 1998, vol. 54, No. 5, pp. 574-583.
Brewer. Regeneration and proliferation of embryonic and adult rat hippocampal neurons in culture. Experimental Neurology. Sep. 1999, vol. 159, No. 1, pp. 237-247.
International Preliminary Examination Report of Nov. 5, 2003 for PCT/US03/01254.
International Preliminary Examination Report of Dec. 23, 2003 for PCT/US03/01014.
International Preliminary Examination Report of Dec. 31, 2003 for PCT/US03/01258.
Pagan, R. et al. Epithelial-mesenchymal transition of cultured rat neonatal hepatocytes is differentially regulated in response to epidermal growth factor and dimethyl sulfoxide. 1997, Hepatology, vol. 25, No. 3, pp. 598-606.
Cheng, C. et al. In vivo proliferation, migration and phenotypic changes of Schwann cells in the presence of myelinated fibers. Neuroscience. Nov. 2002, vol. 115, No. 1, pp. 321-329.
Bayarshaihan, D. et al. Rapid identification of novel chondrocyte-specific gene by RNA differential display. Biochem. And Biophys. Res. Comm. 1995, vol. 220, pp. 449-452.
Sanjo et al. A novel neutrophic pyrimidine compound MS-818 enhances neurotrophic effects of basic fibriblast growth factor. Journal of Neuroscience Research, 1998, vol. 54, pp. 604-612.
Burt et al. Treatment of autoimmune disease by Intense immunosuppressive conditioning and autologous hematopoietic stem cell transplantation. Blood, 1998, vol. 92, No. 10, pp. 3505-3514.
Fukuyama et al., "A synthesized pyrimidine compound, MS-818, promotes walking function recovery from crush injury of the sciatic nerve through its indirect stimulation of Schwann cells" *Restorative Neurology and Neuroscience* 17 (2000) 9-16.
Yoshikawa et al., "The Effect of MS-818, Newly Synthesized Pyrimidine Compound, on Fracture Repair" *Kobe J. Med. Sci.* 46:265-282 (Dec. 2000).
Itoh et al., "The Effect of neurotrophic pyrimidine heterocyclic compounds, MS-818 and MS-430, on the regeneration of injured peripheral nerves" *Restorative Neurology and Neuroscience* 14:265-273 (1999).
Jiang et al., "The effect of MS-818, a pyrimidine compound, on the regeneration of peripheral nerve fibers of mice after a crush injury" *Acta Neuropathol* 90:130-134 (1995).
Yasuhara et al., "The Neurotrophic Pyrimidine Heterocyclic Compound MS-818 Promotes the Angiogenesis Induced by Basic FGF" *Int. J. Clin. Pharm. Res*. XV(5/6) 167-174 (1995).
Koyama et al., "Neurotropic Pyrimidine Heterocyclic Compounds. II. Effects of Novel Neurotropic Pyrimidine Derivatives on Astrocytic Morphological Differentiation" *Biol. Pharm. Bull*. 20(2) 138-141 (1997).
Torigoe et al., "A newly synthesized neurotropic pyrimidine compound, MS-818, may activate migratory Schwann cells in peripheral nerve regeneration" *Brain Research* 787(1998) 337-340.
Watanabe et al., "A Neurotrophic Pyrimidine Compound, MS-818, Enhances EGF-Induced Restoration of Gastric Epithelial Wounds in Vitro" *J. Clin. Gastroenterol* 1988:27(Suppl. 1)S105-S109.
Sugiyama et al., "Acceleration by MS-818 of Early Muscle Regeneration and Enhanced Muscle Recovery after Surgical Transection" *Muscle & Nerve* Feb. 2002 218-229.
Qu et al., Society for Neuroscience Abstracts, "In vivo differentiation and migration properties of mesenchymal stem cells", vol. 27(1), p. 969; 31st Annual Meeting of the Society for Neuroscience; San Diego, California, USA; Nov. 10-15, 2001.
Qu et al., Society for Neuroscience Abstracts Viewer and Itinerary Planner, "A seven fold increase in neural stem cell population is induced by pyrimidine derivatives MS-818", Abstract No. 825.8, 32nd Annual Meeting of the Society for Neuroscience; Orlando, Florida, USA; Nov. 2-7, 2002.
Ferrari et al., (1998), Muscle regeneration by bone marrow-derived myogenic progenitors, Science 279: 1528.
Gussoni et al., (1999), Dystrophin expression in the mdx mouse restored by stem cell transplantation, Nature 401: 390.
Petersen et al., (1999), Bone marrow as a potential source of hepatic oval cells, Science 284: 1168.

Pereira et al., (1995) Cultured adherent cells from marrow can serve as long-lasting precursor cells for bone cartilage and lung in irradiated mice PNAS 92:4857.

Procktop et al., (1997), Marrow stromal cells as stem cells for nonhematopoietic tissues, Science 276:71.

Pittenger et al., (1999), Multilineage potential of adult human mesenchymal stem cells, Science 284:143.

Kessler PD, (1999), Myoblast cell grafting into heart muscle: cellular biology and potential applications, Annu. Rev. Physiol. 61:219.

Kopen et al., (1999), Marrow stromal cells migrate throughout forebrain and cerebellum, and they differentiate into astrocytes after injection into neonatal mouse brains, Proc. Nat'l. Acad. Sci., 96:10711-10716.

Kohyama, Jun, et al., "Brain From Bone: Efficient 'Meta-Differentiation' of Marrow Stroma-Derived Mature Osteoblasts to Neurons with Noggin or A Demethylating Agent," Differentiation, 2001, vol. 68, pp. 235-244.

Awaya, Akira, et al., "Neurotropic Pyrimidine Heterocyclic Compounds. I. The Newly Synthesized Pyrimidine Compounds Promote Neurite Outgrowth of GOTO and Neuro 2a Neuroblastoma Cell Lines, and Potentiate Nerve Growth Factro (NGF)-Induced Neurite Sprouting of PC 12 Cells," Bio. Pharm. Bull., 1993, 16(3), pp. 248-253.

Noda' Masayuki' et al., "Increase of Nerve Regeneration Capacity by New Neurotrophic . Pyrimidine Derivative MS-430," Gen. Pharmac., 1998, vol. 31, No. 5, pp. 821-824.

Ohnishi, Akio, et al., "The Effect of MS-430, a Synthetized Pyrimidine Compound, on regeneration of Nerve Fibers of Rats after Crush Injury," J UOEH, 1995, 17(2), pp. 131-139.

Sager, Ruth, et al., "Pre-Adipocyte Determination either by Insulin or by 5-Azacytidine," Proc. Natl. Acad. Sci., Cell Biology, 1982, vol. 79, pp. 480-484.

* cited by examiner

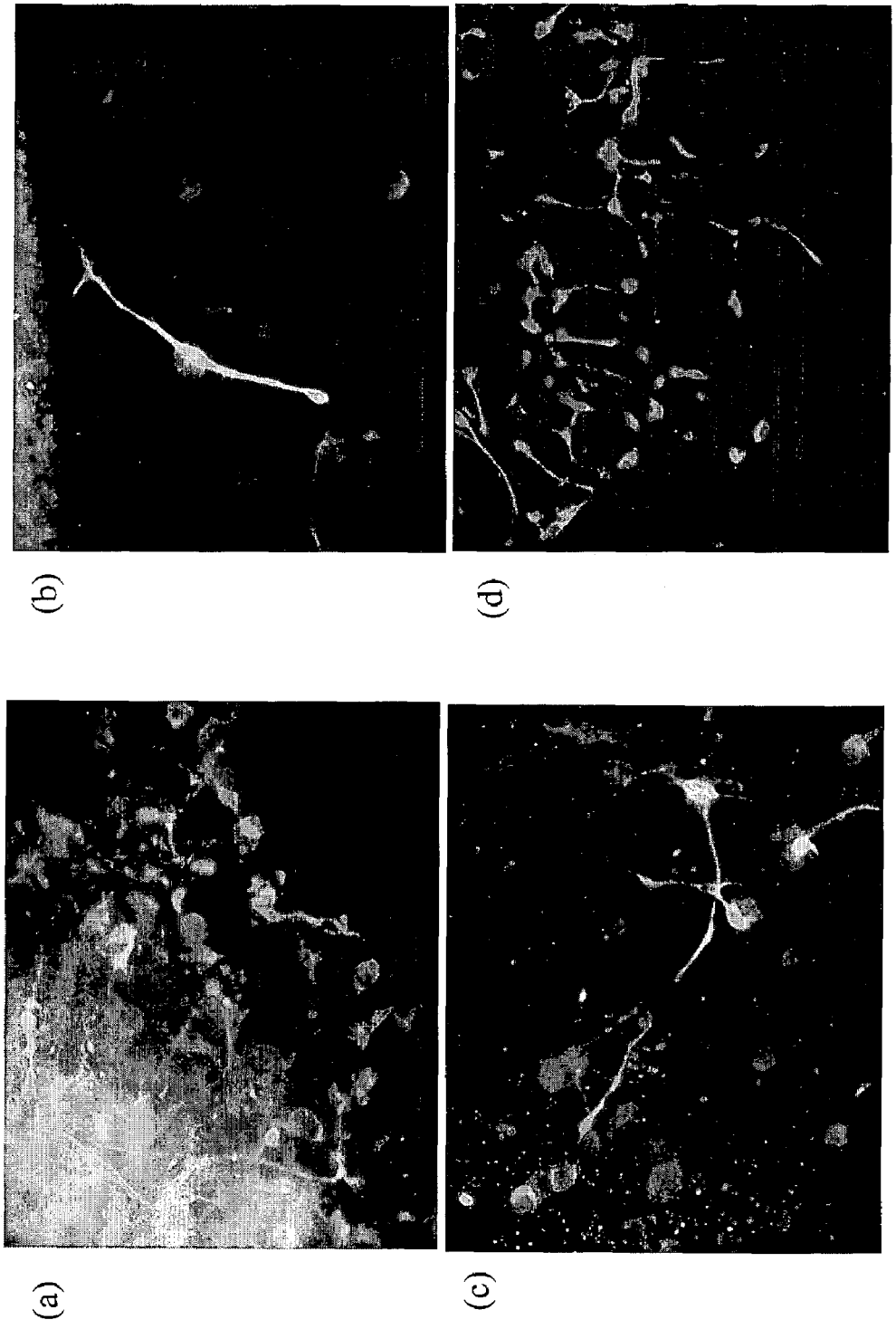
Figure 7 (II)

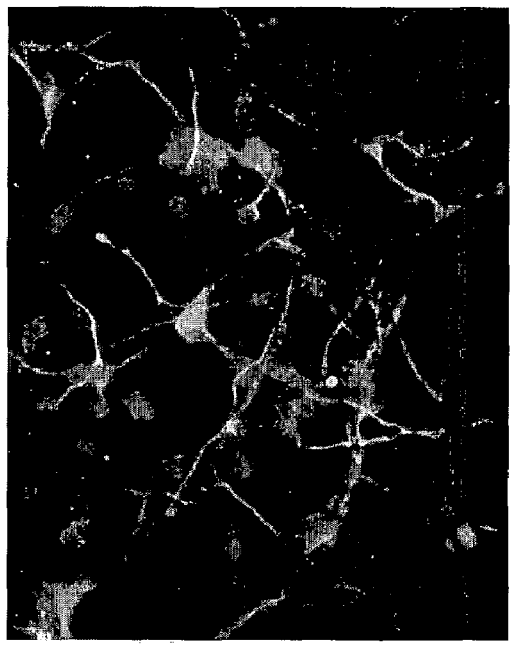
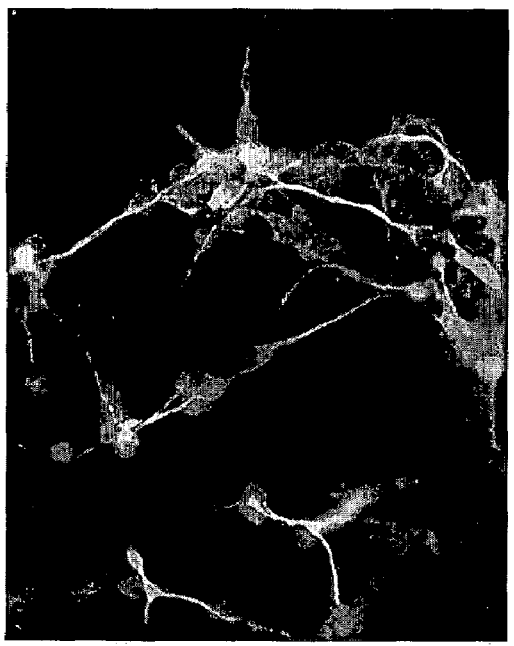
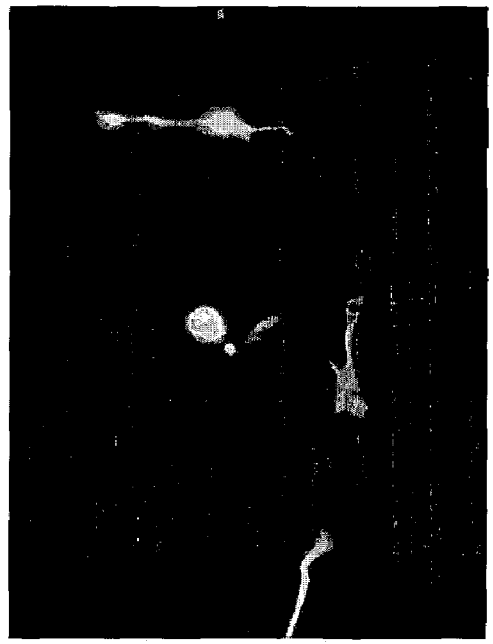
Figure 8 (II)

MAMMALIAN MULTIPOTENT NEURAL STEM CELLS AND COMPOSITIONS, METHODS OF PREPARATION AND METHODS OF ADMINISTRATION THEREOF

This application is related to U.S. Provisional Patent Applications, Ser. No. 60/348,473, filed Jan. 14, 2002, and Ser. No. 60/357,783, filed Feb. 19, 2002, and Ser. No. 60/376,257, filed Apr. 29, 2002, and Ser. No. 60/381,138, filed May 8, 2002, and Ser. No. 60/404,361, filed Aug. 19, 2002, and Ser. No. 60/430,381, filed Dec. 2, 2002, the disclosures of each of which are expressly incorporated by reference herein.

This invention was made with support from the U.S Government through the National Institutes of Health, grant no. R03-AG19874. The government has certain rights in this invention.

BACKGROUND OF THE INVENTION

1. Field of the Invention

This invention relates to novel mammalian multipotent neural stem cells (MNSCs), compositions thereof, and methods of preparing and administering such cells. In one aspect, the invention relates to methods of making one or a plurality of mammalian multipotent stem cells that can form a cluster. In another aspect, the invention relates to cells prepared according to the methods of the invention. In another aspect, the invention relates to pharmaceutical compositions comprising one or a plurality of mammalian multipotent stem cells that can form a cluster of the invention. In another aspect, the invention relates to cellular preparations for cell or tissue regeneration comprising one or a plurality of mammalian multipotent stem cells that can form a cluster of the invention. In another aspect, the invention relates to a method for regenerating cells or tissue comprising administering one or a plurality of mammalian multipotent stem cells that can form a cluster of the invention to an animal in need thereof. In another aspect, the invention relates to a method for treating an animal or human having a neurological or corporal deficit comprising the step of administering one or a plurality of mammalian multipotent stem cells that can form a cluster of the invention or terminally differentiated cells produced according to the invention to an animal, including human, in need thereof. In another aspect, the invention relates to a method of making and using a terminally differentiated cell utilizing one or a plurality of mammalian multipotent stem cells that can form a cluster of the invention.

2. Background of the Related Art

Stem cells are often defined as self-renewing and multipotent, with the ability to generate diverse types of differentiated cells. As such, they show promise in the treatment of neurological and corporal deficits, or any loss or diminishment of tissue function due to age, disease, trauma or other factor. However, such treatments have faced significant hurdles that have yet to be substantially overcome.

NSCs and Neurological Deficits

Because one important focus of stem cell replacement therapies has been neurological disorders, neural stem cells, and particularly fetal neural stem cells, have been a major research target. During development of the central nervous system (CNS), multipotent neural stem cells (MNSCs), also known as multipotent precursor cells (MPCs) or neural stem cells (NSCs), proliferate, giving rise to transiently dividing progenitor cells that eventually differentiate into the cell types that compose the adult brain, including neurons, astrocytes and oligodendrocytes. NSCs have been isolated from several mammalian species, including, mice, rats, pigs and humans. See, e.g., International Application, Publication Nos. WO 93/01275, WO 94/09119, WO 94/10292, WO 94/16718 and Cattaneo et al., 1996, *Mol. Brain Res.* 42: 161-66. NSCs from the embryonic and adult rodent central nervous system (CNS) have been isolated and further propagated in vitro in a variety of culture systems. See, e.g., Frolichsthal-Schoeller et al., 1999, *NeuroReport* 10: 345-351; Doetsch et al., 1999, *Cell* 97: 703-716. NSCs from the human fetal brain have been cultured using serum-free medium supplemented with epidermal growth factor (EGF) and/or basic fibroblast growth factor (bFGF). See, e.g., Svendsen et al., 1998, *J. Neuroscience Methods* 85: 141-152; Carpenter et al., 1999, *Experimental Neurology* 158: 265-278. NSCs cultured utilizing these, serum-free, mitogen-supplemented methods generally form substantially undifferentiated, clustered aggregates. Upon removal of the mitogen(s) and provision of a substrate, the stem cells differentiate into neurons, astrocytes and oligodendrocytes.

While the synaptic connections involved in neural circuits are continuously altered throughout the life of the individual, due to synaptic plasticity and cell death, neurogenesis, the generation of new neurons, was thought to be complete early in the postnatal period. The discovery of NSCs in adult brain (see, e.g., Alvarez-Buylla et al., 1997, *J. Neurobiology* 33: 585-601; Gould et al., 1999, *Science* 286: 548-552) has brought significant changes in the theory on neurogenesis as the presence of MNSCs in the adult brain suggests that regeneration of neurons can occur throughout life. Nevertheless, age, physical and biological trauma or neurodegenerative disease-associated loss of brain function, herein referred to as a "neurological deficit," can far outweigh any potential restorative effects due to endogenous neurogenesis. As a result, transplantation of NSCs is a potentially valuable treatment for those suffering from the loss of, or loss of appropriate, brain function due to age, physical and biological trauma or neurodegenerative disease; a neurological deficit.

Due to the advancing average age of the population, and concomitantly increased incidence of neurological deficit that: accompanies advancing age, treatment of neurodegenerative diseases has become a major concern. Such diseases, including Alzheimer's disease, Huntington's chorea and Parkinson's disease, have been linked to neural degeneration at specific locations in the brain, leading to the inability of the brain region to synthesize and releases neurotransmitters that are vital to neural signaling.

Neurodegeneration also encompasses many conditions and diseases, age-related or not, that result in neural loss. These conditions include CNS trauma, such as stroke and epilepsy, as well as diseases that result in neural loss, including amyotrophic lateral sclerosis and cerebral palsy.

Degeneration in a brain region known as the basal ganglia can lead to diseases with varied and different cognitive and motor symptoms, depending on the exact location of the lesion. The basal ganglia consists of many separate regions, including the striatum (which consists of the caudate and putamen), the globus pallidus, the substantia nigra, substantia innominata, ventral pallidum, nucleus basalis of Meynert, ventral tegmental area and the subthalamic nucleus.

Degeneration in the basal ganglia can lead to motor deficits. For example, Huntington's chorea is associated with degeneration of neurons in the striatum, which leads to involuntary jerking movements. Degeneration of a small region called the subthalamic nucleus is associated with violent flinging movements of the extremities in a condition called ballismus, while degeneration in the putamen and globus pallidus are associated with a condition of slow writhing movements or athetosis. In Parkinson's disease, degeneration is seen in another area of the basal ganglia, the substantia nigra par compacta. This area normally sends dopaminergic-connections to the dorsal striatum, which are is? important in regulating movement. Therapy for Parkinson's disease has centered upon restoring dopaminergic activity to this circuit.

Alzheimer's disease patients exhibit a profound cellular degeneration of the forebrain and cerebral cortex. Further, a localized area of the basal ganglia, the nucleus basalis of Meynert, appears to be selectively degenerated. This nucleus normally sends cholinergic projections to the cerebral cortex that are thought to participate in cognitive functions including memory.

The objective of most CNS therapies is to regain the particular chemical function or enzymatic activity lost due to cellular degeneration. Administration of pharmaceutical compositions has been the main treatment for CNS dysfunction. Unfortunately, this type of treatment has many complications, including the limited ability to transport drugs across the blood-brain barrier, and drug-tolerance acquired by patients to whom these drugs are administered for long-periods.

Transplantation of multipotent stem cells may avert the need not only for constant drug administration, but also for complicated drug delivery systems necessitated by the blood-brain barrier. In practice, however, significant limitations have been found in this technique as well. First, cells used for transplantation that carry cell surface molecules of a differentiated cell from a donor can induce an immune reaction in the recipient, a problem that is exacerbated by the physical damage caused by injection of cells directly into the affected area of the brain. In addition, the neural stem cells must be at a developmental stage where they are able to form normal neural connections with neighboring cells. For these reasons, initial studies on neurotransplantation centered on the use of fetal cells.

Mammalian fetal brain tissue has proven to have reasonable survival characteristics upon immediate transplantation. Increased survival capability of fetal neurons is thought to be due to the reduced susceptibility of fetal neurons to anoxia compared to adult neurons. An additional factor favoring survival of fetal cells is the lack of cell surface markers on fetal cells, whose presence may lead to rejection of grafted tissue from adults. However, although the brain is considered an immunologically privileged site, some rejection of even fetal tissue can occur. Therefore, the ability to use heterologous fetal tissue is limited by tissue rejection and the need for immunosuppressant drugs.

The use of large quantities of aborted fetal tissue presents other difficulties as well. Fetal CNS tissue is composed of more than one cell type, and thus is not a well-defined tissue source. In addition, there are doubts as to whether an adequate and constant supply of fetal tissue would be available for transplantation. For example, in the treatment of MPTP-induced Parkinsonism, tissue from as many as 6 to 8 fetuses can be required for successful implantation into the brain of a single patient. There is also the added problem of the potential for contamination during fetal tissue preparation. Since these tissue may already be infected with a bacteria or virus, expensive diagnostic testing is required for each fetus used. Even comprehensive diagnostic testing might not uncover all infected tissue. For example, there can be no guarantee that a sample is HIV-free, because antibodies, to the virus are generally not present until several weeks after infection.

In addition to fetal tissue, there are other potential sources of tissue for neurotransplantation, including cell lines and genetically engineered cell types, but both sources present problems. Cell lines are immortalized cells that are derived, inter alia, by transformation of normal cells with an oncogene or by the culturing of cells in vitro with altered growth characteristics. Moreover, adverse immune response potential, the use of retroviruses to immortalize cells, the potential for the reversion of these cells to an amitotic state, and the lack of response by these cells to normal growth-inhibiting signals make such cell lines sub-optimal for widespread use.

Another approach to neurotransplantation involves the use of genetically engineered cell types or gene therapy. However, there still exists a risk of inducing an immune reaction with these cells. In addition, retrovirus mediated transfer may result in other cellular abnormalities. Also, cell lines produced by retrovirus-mediated gene transfer have been shown to gradually inactivate their transferred genes following transplantation and further may also not achieve normal neural connections with the host tissue.

While currently available transplantation approaches represent an improvement over other available treatments for neurological disorders, they suffer from significant drawbacks. The inability in the prior art of the transplant to fully integrate into the host tissue, and the lack of availability of suitable cells in unlimited amounts from a reliable source for grafting are significant limitations of neurotransplantation. Studies utilizing intra-tissue injection of dissociated and partially differentiated NSCs have shown little promise (see, e.g., Benninger et al., 2000, *Brain Pathol.* 10: 330-341; Blakemore et al. 2000, *Cell Transplant* 9: 289-294; Rosser et al., 2000, *Eur. J. Neurosci.* 12: 2405-2413; Rubio et al., 2000, *Mol. Cell Neurosci.* 16: 1-13). The results have generally been poor because, among many considerations, the dissociation of clusters of NSCs is known to cause immediate senescence of NSCs and increase the vulnerability of NSCs in culture. See, e.g., Svendsen et al., 1998, *J. Neurosci. Methods* 85: 141-152. Further, regardless of adverse immune responses due to foreign tissue being introduced into the brain, the trauma caused by the physical introduction of cells directly into the damaged area can induce the recruitment of immune cells by the host that can eliminate the transplanted cells. Thus, significant problems with the use of NSCs to ameliorate neurological deficits remain.

As described herein, neurological deficits also include non-brain tissues such as, for example, the eye and spinal cord. In addition, corporal deficits are a target for amelioration utilizing multipotent stem cells. A "corporal deficit" is a disorder caused by a wide variety of diseases and injuries, resulting in trauma, malfunction, degeneration or loss of muscle such as, for example, cardiac muscle due to myocardial infarction. Other examples include malfunction, degeneration or loss of other cells and tissues apart from those discussed in the neurological deficit section above such as, for example, internal organs. For example, liver function can be adversely affected by, among other things, disease (e.g., cirrhosis or hepatitis), trauma or age. The problems described above in using NSCs to remedy neurological deficits of the brain also apply to neurological deficits in other tissues, such as the eye, and corporal deficits.

There exists a need in the art for improved methods for introducing multipotent neural stem cells to diseased, aged or damaged tissue such that the cells properly migrate and differentiate and a neurological or corporal deficit is improved or remedied as a result. In addition, there remains a need for methods of use or administration of the multipotent stem cells of the invention, or pharmaceutical preparations thereof, to the affected, damaged or degenerated tissue, wherein the stem cells can differentiate in a manner appropriate for the host tissue and enable the replacement of damaged cells, repair of damages tissue and, optionally, amelioration of functional loss. There also remains a need in the art for a reliable source of unlimited numbers of cells for transplantation, particularly cells that are specifically adapted for and capable of proliferation, migration, and differentiation in mammalian brain or other tissues when introduced thereto. Furthermore, there exists a need in the art for methods for repairing damaged neural and other tissue in as non-invasive a fashion as possible, especially by inducing multipotent stem cells to proliferate and differentiate in vivo into, for example, neurons, astrocytes, and oligodendrocytes in the brain or, for example, rod or cone photoreceptor cells, horizontal cells, bipolar cells, amacrine cells, ganglion cells, Muller cells, and nerve cells in the eye. Further, there remains a need for a method of making a terminally differentiated cell from and a method of administering the one or plurality of mammalian multipotent stem cells that can form a cluster produced according to the methods of the invention.

SUMMARY OF THE INVENTION

This invention provides methods for producing multipotent stem cells, particularly neural stem cells, and cells produced by those methods. In particular, the invention provides reagents and methods for efficiently producing neural stem cells that can be reintroduced into an animal in need thereof to alleviate neurological or corporal disorders.

In a first aspect, the invention provides methods for preparing one or a plurality of mammalian multipotent stem cells that can form a cluster comprising the steps of isolating mammalian neural stem cells (MNSCs) derived from mammalian neural tissue containing at least one neural stem cell; culturing said cells in a cell culture media under conditions that permit proliferation of the neural stem cells in vitro;; and harvesting the cluster of mammalian stem cells produced in above, wherein said one or plurality of mammalian multipotent stem cells that can form a cluster is adapted for proliferation, migration and differentiation in mammalian tissue when introduced thereto. In certain embodiments, the methods comprise the additional steps of culturing said cells in a cell culture media comprising an effective amount of substituted deoxynucleotide or deosynucleoside compound for an effective period. In certain embodiments, the inventive methods further comprise the step of contacting a MNSC with substituted deoxynucleotide of deoxynucleoside compound in an uncoated flask or a flask that has been treated to repel the cells. In further embodiments, the MNSC cell is further contacted with a growth factor such as fibroblast growth factor, epidermal growth factor or a combination thereof. Alternatively, the MNSCs are contacted additionally with heparin.

Exemplary substituted deoxynucleotide or deoxynucleoside compounds as provided by the invention include but are not limited to halogen-substituted (halo-substituted) deoxynucleotides or deoxynucleosides, such as, for example, bromodeokyunridine, iododeoxyuridine, bromodeoxyguanosine, iododeoxycytosine as well as alkyl-substituted species such as, for example, methyldeoxythymidine. A most preferred species is bromodeoxyuridine (BrdU). In certain embodiments, the mammalian neural stem cells are obtained from any tissue containing stem cells including but not limited to zygote, blastocyst, embryo, fetus, infant juvenile or adult, and optionally, a human species of any of the preceding embodiments, whether naturally occurring or engineered. Said cells in some embodiments comprise neural-lineage cells such as neural stem cells, neurons, oligodendrocytes and astrocytes. As provided herein, the methods of the invention provide one or a plurality of mammalian multipotent stem cells that can form a cluster.

In a second aspect, the invention provides one or a plurality of mammalian multipotent stem cells that can form a cluster that preferably comprise less than about 50 percent, more preferably less than about 25 percent, even more preferably less than about 10 percent, even more preferably less than about 5 percent, and even more preferably less than about 1 percent differentiated neural stem cells. In certain embodiments, the invention in this aspect provides a preparation for cell or tissue regeneration comprising, as an active ingredient, one or a plurality of mammalian multipotent stem cells that can form a cluster produced according to the methods of the invention. In other related embodiments, the invention provides terminally differentiated cells produced from the one or plurality of mammalian multipotent stem cells that can form a cluster.

In yet further aspects of the invention are provided pharmaceutical compositions comprising said one or plurality of mammalian multipotent stem cells that can form a cluster prepared according to the methods of the invention and a pharmaceutically-acceptable carrier or excipient. The invention provides such pharmaceutical compositions comprising said one or plurality of mammalian multipotent stem cells that can form a cluster that are tissue stem cells for use in cell or tissue regeneration or for correcting a disease or disorder in an tissue or animal in need thereof. In certain embodiments, the one or plurality of mammalian multipotent neural stem cells of the invention are neural stem cells for use in correcting, treating or ameliorating a neurological disease or disorder in an animal in need thereof. In certain embodiments, the invention in this aspect provides a preparation for cell or tissue regeneration comprising, as an active ingredient, one or a plurality of mammalian multipotent stem cells; that can form a cluster produced according to the methods of the invention.

Thus, the invention also provides methods for using the pharmaceutical compositions provided herein to treat an animal in need thereof by administering the one or plurality of mammalian multipotent neural stem cells of the invention thereto. Preferably, the animal has a corporal or neurological deficit that can be treated or ameliorated by administration of the one or plurality of mammalian multipotent neural stem cells of the invention, such as a deficit caused by a neurodegenerative disease, a traumatic injury, a neurotoxic injury, ischemia, a developmental disorder, a disorder affecting vision, an injury or disease of the spinal cord, a demyelinating disease, an autoimmune disease, an infection, an inflammatory disease, or corporal disease, disorder, injury, trauma, malfunction, degeneration or loss. In preferred embodiments, the one or plurality of mammalian multipotent neural stem cells is capable of migrating to an area of tissue damage, differentiate in a tissue-specific manner and function in a manner that reduces the neurological or corporal deficit. As provided by the methods of the invention herein, the cells are administered by injecting the one or plurality, of mammalian multipotent neural stem cells with a syringe, inserting the one or plurality of mammalian multipotent neural stem cells with a catheter or surgically implanting the mammalian neural stem cells. In certain embodiments, the one or plurality of mammalian multipotent neural stem cells are injected with a syringe into a body cavity that is fluidly-connected to the area of neurological or corporal deficit. In certain preferred embodiments, the body cavity is a brain ventricle. In other embodiments, the one or plurality of mammalian multipotent neural stem cells are inserted with a catheter into a body cavity that is fluidly-connected to the area of neurological or corporal deficit. In certain preferred embodiments, the body cavity is a brain ventricle. In still further additional embodiments, the one or plurality of mammalian multipotent neural stem cells are surgically implanted into a body cavity that is fluidly-connected to the area of neurological or corporal deficit. In certain preferred embodiments, the body cavity is a brain ventricle. The one or plurality of mammalian multipotent neural stem cells can also alternatively be inserted using a syringe or catheter or surgically implanted directly at the site of the neurological or corporal deficit or systemically (e.g., intravenously). In certain related embodiments, the invention provides a method for treating a patient having a neurological; deficit or corporal deficit with terminally differentiated cells of the invention, comprising the step of administering said terminally differentiated cells to an animal having a neurological deficit or corporal deficit.

In still further aspects, the invention provides a method of making a retinal cell, the method comprising contacting a neural stem cell; before or during differentiation with an effective amount of growth factor selected from the group consisting of TGF-b3, CNTF and IGF-1, or a combination of two or more said group, for an effective period, wherein the growth factor-contacted neural stem cells become capable of differentiating into retinal cells. The invention also provides the cells produced according to these methods, which can be used to treat a patient, animal or human, having a neurological deficit, where the retinal cell produced according to these methods, when administered, are capable of migrating to an area of tissue damage, differentiating in a tissue-specific manner and functioning in a manner that reduces the neurological deficit. In preferred embodiments, the retinal cells produced according to these methods can be used in treating a neurological deficit relating to tissues of the eye.

Thus, the present invention provides what is needed in the art: one or a plurality of novel mammalian multipotent neural stem cells (MNSCs) that can form a cluster, compositions thereof, and methods of preparing and administering the cells to diseased, aged or damaged tissue, wherein the cells properly migrate and differentiate and a neurological or corporal deficit is improved or remedied as a result. More specifically, the invention provides methods of making one or a plurality of mammalian multipotent neural stem cells that can form a cluster; cells prepared according to the methods of the invention; pharmaceutical compositions comprising one or a plurality of mammalian multipotent neural stem cells that can form a cluster of the invention; cellular preparations for cell or tissue regeneration comprising one or a plurality of mammalian multipotent neural stem cells of the invention; a method for regenerating cells or tissue comprising administering one or a plurality of the mammalian multipotent neural stem cells of the invention; a method for treating a patient having a neurological or corporal deficit comprising administering one or a plurality of mammalian multipotent neural stem cells of the invention; a method of administering one or a plurality of mammalian multipotent neural stem cells that can form a cluster produced according to the method of the invention; a method of making a terminally differentiated cell utilizing one or a plurality of mammalian multipotent neural stem cells of the invention; and methods of making retinal cells from neural stem cells, methods of use thereof and the cells produced according to those methods.

Specific embodiments of the present invention will become evident from the following more detailed description of certain preferred embodiments and the claims.

BRIEF DESCRIPTION OF THE DRAWINGS

FIG. 8 (II) immunohistochemistry of NSCs treated with certain growth factors were able to differentiate to retinal cells upon transplantation to the eye. NSCs grown in basal media differentiated to opsin-expressing cells in vivo after exposure to IGF-1, TGF-b3 or CNTF for four days. Cells were treated with 20 ng/ml of IGF-1, 100 ng/ml of TGF-b3, or 10 ng/ml of CNTF prior to transplantation into rat eye. Double immunofluorescence staining with GFAP (red), opsin (green), markers for astrocytes and retinal cells, respectively. The blue signal represents counter staining for nuclei by DAPI. The transplanted NSCs can differentiate into retinal cells through the action of the growth factors.

DETAILED DESCRIPTION OF PREFERRED EMBODIMENTS

Figure 1:
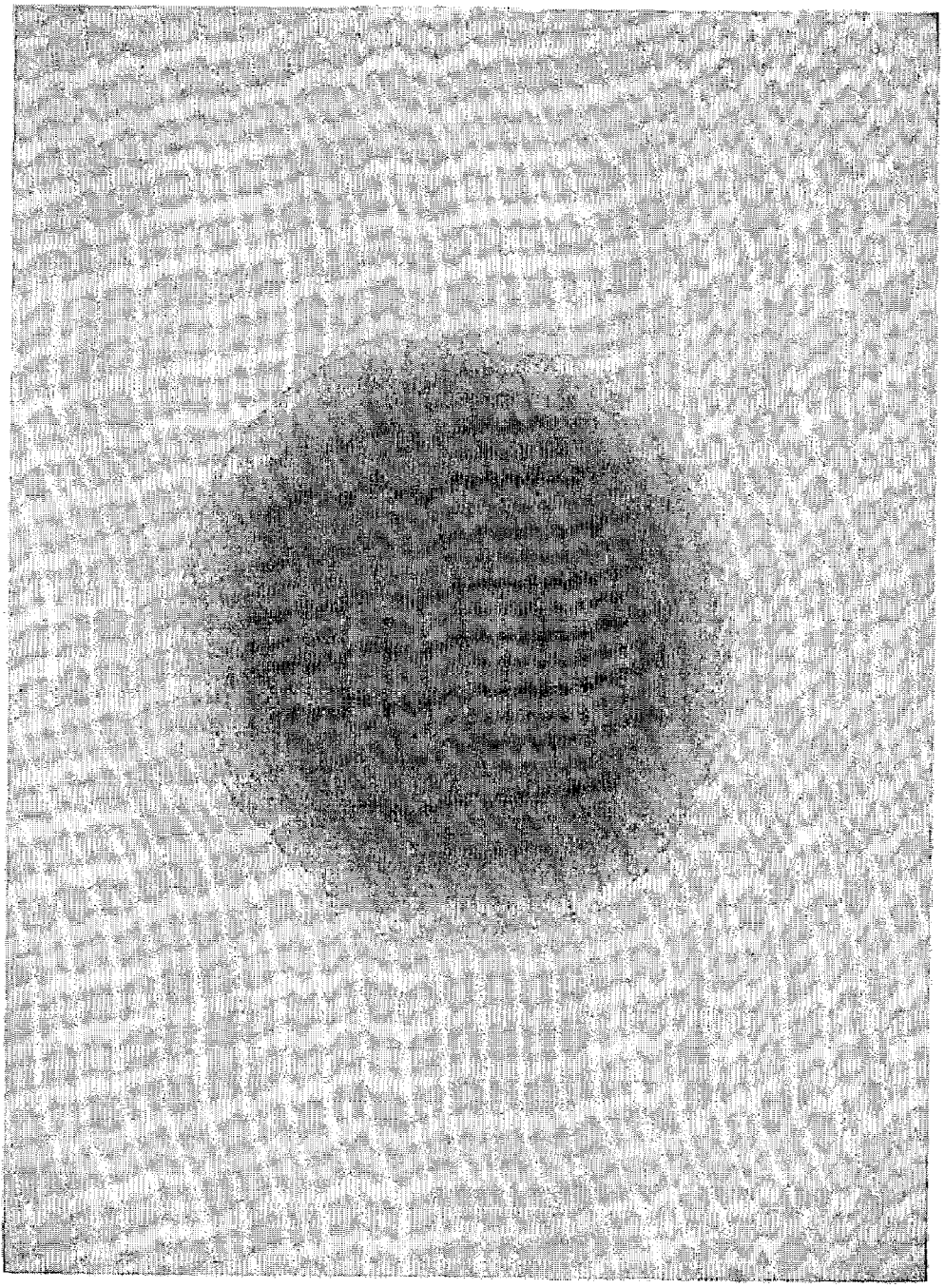
FIG. 1. shows a phase contrast photomicrograph of a floating, aggregated cluster of cells, characteristic of certain embodiments of the cells of the invention.

This invention provides one or a plurality of mammalian multipotent neural stem cells that can form a cluster and are specially adapted for proliferation, migration and differentiation in mammalian tissue when introduced thereto. Such cells are capable of differentiating in a tissue specific manner, particularly neural stem cells capable of differentiating inter alia, in brain tissues and that can be administered to an animal in need thereof.

As disclosed in further detail herein, the inventive: methods provide for culturing mammalian neural stem cells obtained, inter alia, from somatic tissue sources, and producing multipotent neural stem cells specially adapted for proliferation, migration and differentiation therefrom. In one aspect, this effect is achieved by culturing mammalian neural stem cells in the presence of a substituted deoxynucleotide or deoxynucleoside compound. Exemplary substituted deoxynucleotide or deoxynucleoside compounds include but are not limited to halogen-substituted (halo-substituted) deoxynucleotide or deoxynucleoside species such as, for example, bromodeoxyuridine, iododeoxyuridine, bromodeoxyguanosine, iododeoxycytosine as well as alkyl-substituted species such as, for example, methyldeoxythymidine. A most preferred species is bromodeoxyuridine (BrdU). BrdU is a thymidine analog that was originally, produced for chemotherapy. It is known to regulate gene expression and cellular differentiation of some cell types. Since BrdU; and other substituted deoxynucleotide or deoxynucleoside compounds are incorporated into the nuclei of proliferating cells and are easy to detect by immunostaining, it has been used for detecting proliferating cells, such as stem cells; however, its biological effects on stem cells have not been appreciated, understood or disclosed in the art.

The invention relates to methods of making mammalian multipotent neural stem cells specially adapted for proliferation, migration and differentiation from mammalian neural stem cells (NSCs), as well as methods of treatment and use of the specially adapted MNSCs, and the specially adapted MNSCs themselves. Thus, the present invention provides a means to treat neurological and corporal deficits.

As used herein, the terms "multipotent neural stem cells (MNSCs).", "neural stem cells. (NSCs)," "multipotent precursor cells (MPCs)" and "neural progenitor cells (NPCs)" refer to undifferentiated, multipotent cells of the CNS. Such terms are commonly used in the scientific literature. MNSCs can differentiate into tissue-specific cell types, for example astrocytes, oligodendrocytes, and neurons when transplanted in the brain. MNSCs of the invention are distinguished from natural MNSCs by their adaptation for proliferation, migration and differentiation in mammalian host tissue when introduced thereto.

As used herein, the term "cluster" refers to a group of two or more cells. A cluster can take any shape but such groups of non-terminally differentiated multipotent cells often assume a generally spherical shape. The clusters can comprise the progeny of a single multipotent neural stem cell or small cluster of primary cells.

As used herein, the terms "effective amount" and "therapeutically effective amount" each refer to the amount of reagent used to support the desired activity. In the case of the cells prepared and delivered according to the invention, an effective amount is an amount necessary to support an observable level of one or more biological activities of MNSC as set forth herein. Regarding substituted deoxynucleotide or deoxynucleoside compounds, an effective amount can be between about 10 nanomolar and 100 micromolar, or more preferably between about 2 and 50 micromolar, or even more preferably about 10 micromolar. Regarding growth factors, an effective amount can be between about 1 ng/ml to 1 ug/ml, or more preferably between about 5 ng/ml to 500 ng/ml, or even more preferably between about 10 ng/ml to 100 ng/ml, or even more preferably about 50 ng/ml.

An "effective period" as used herein refers to the time period necessary for the reagents and cells of the invention to accomplish their specified activities. For example, less developmentally potent cells can be contacted with a substituted deoxynucleotide or deoxynucleoside compound for an effective period to make them more developmentally potent. An effective period for contact with a substituted deoxynucleotide or deoxynucleoside compound, as referred to herein, can be between 1 to 10 days, or more preferably between about 1 to 5 days, or even more preferably between about 2 to 3 days. An effective period for growth factor contact, as with the substituted deoxynucleotide or deoxynucleoside compounds, can be between about 1 to 10 days, or more preferably between about 1 to 7 days, or even more preferably between about 2 to 5 days.

The term "pharmaceutically acceptable carrier" or "physiologically acceptable carrier" as used herein refers to one or more formulation materials suitable for accomplishing or enhancing the successful delivery of the pharmaceutical composition of the specially adapted MNSCs prepared and delivered according to the invention.

As used herein, "ameliorating the effects caused by age, physical and biological trauma and degenerative disease" and the like refers to the diminution of the detrimental effects of damaged or degenerated tissue due to the use or administration of an effective amount of the specially adapted MNSCs of the invention, or pharmaceutical preparations thereof, to the affected, damaged or degenerated tissue, wherein the neural stem cells can differentiate in a manner appropriate for the host tissue and enable the replacement of damaged cells, repair of damages tissue and reduction of structural or functional loss. For example, the neurological effects of events, diseases or processes that result in the loss of some degree of brain function or proper brain function. Such amelioration is affected through the administration to the animal of an effective amount of the specially adapted MNSCs of the invention or pharmaceutical compositions thereof.

The invention also provides pharmaceutical compositions of the MNSCs of the invention and methods of delivery into the brain and other tissues thereof. The invention also provides methods of abating or remedying the effects of brain or other tissue disease or dysfunction caused by the loss of, or loss of appropriate, brain or other tissue function due to age, physical or biological trauma or neurodegenerative disease.

The invention provides specially adapted MNSCs capable of differentiating in a tissue specific manner, and the MNSCs can take and be administered in the form of clusters. Cells can be obtained in many ways and from many tissues, for example, from donor tissue by dissociation of individual cells from the connecting extracellular matrix of the tissue or from commercial sources of NSCs (e.g., BioWhittaker, Walkersville, Md., CC-2599). Tissue from brain is removed using, sterile procedures, and the cells are dissociated using any method known in the art including treatment with enzymes such as trypsin, collagenase and the like, or by using physical methods of dissociation such as mincing or treatment with a blunt instrument. Dissociation of neural cells can be carried out in tissue culture medium; the medium for dissociation of juvenile and adult cells is low calcium artificial cerebral spinal fluid (aCSF) having a formula as aCSF (124 mM NaCl, 5 mM KCl, 1.3 mM $MgCl_2$, 2 mM $CaCl_2$, 26 mM $NaHCO_3$, and 10 mM D-glucose) except that $MgCl_2$ is present at a concentration of 3.2 mM and $CaCl_2$ at a concentration of 0.1 mM. Dissociated cells are centrifuged at low speed, between 200 and 2000 rpm, usually between 400 and 800 rpm, the suspension medium is aspirated, and the cells are then resuspended in culture medium suspension cultures are preferred if large numbers of undifferentiated neural stem cell progeny are desired. Cell suspensions are seeded in any receptacle capable of sustaining cells, preferably uncoated flask or a flask that has been treated to repel the cells, culture plates or roller bottles that inhibit contact-dependent stem cell differentiation.

Growth of NSCs under the above culture conditions induces or permits these cells to form undifferentiated clusters (shown in FIG. 1). These clusters are: optimally grown at a density of approximately 50 spheres per T75 flask in 20 mL of the growth medium consisting of, for example, DMEM/ HAMS F12 (at about 3:1; Gibco, BRL, Burlington, ON), supplemented with an antibiotic-antimycotic mixture (1:100, penicillin G, streptomycin sulfate, amphotericin B; Gibco);), B27 (1:50, GIBCO), human recombinant FGF-2 and EGF (20 ng/ml each, R&D Systems, Minneapolis, Minn.) and heparin (5 μg/mL, Sigma, St. Louis, Mo.). The cultures are kept in a $CO_2$ incubator (about 5% $CO_2$) at 37° C. To facilitate optimal growth conditions, any clusters of two or more cells are sectioned into quarters approximately every 14 days and fed by replacing 50% of the medium approximately every 4-5 days. These conditions permit rapid and continual growth of NSCs that can be expanded indefinitely while retaining: their multipotent character. As with most eukaryotic cells, conditions for culturing should be as close as possible to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., land more preferably between about 35° C. to about 37° C. In the case of neural stem cells (NSCs), after more than three years of serum-free propagation, NSCs prepared and maintained as disclosed herein continue to exhibit multipotent character. If in vitro differentiation is desired, the cells can be replated in culture dishes in, for example, serum-free basal medium Eagle (BME), which contains Earle's salt and L-glutamine. The cells can be cultured for about 5 days in the absence of FGF-2, EGF or other extrinsic differentiation factors. When induced to differentiate in this way, these cultured NSCs exhibit characteristic morphollogies of neurons or astrocytes when immunohistochemically stained with b-III tubulin (a neural cell marker) or glial fibrillary acidic protein (GFAP, an astrocyte marker).

As disclosed above, the stem cell culture medium as used in the invention is preferably supplemented with at least one proliferation-inducing growth factor. A growth factor, as defined herein, refers to a protein, peptide or other molecule having a growth, proliferative, or trophic effect on the specially adapted MNSCs and MNSC progeny of the invention. Growth factors that are used for inducing proliferation include any trophic factor that allows NSCs to proliferate, including any molecule that binds to a receptor on the surface of the cell to exert a trophic, or growth-inducing effect on the cell. Exemplary proliferation-inducing growth factors include epidermal growth factor (EGF), insulin-like growth factor-1 IGF-1), ciliary neurotrophic factor (CNTF), amphiregulin, acidic fibroblast, growth factor (AFGF or FGF-1); basic fibroblast growth factor (bFGF or FGF-2), transforming growth factor alpha (TGFa), and combinations thereof. Preferred proliferation-inducing growth factors include EGF and FGF or a combination thereof. Growth factors are usually added to the culture medium at concentrations of between about 1 fg/mL to 1 mg/mL. Concentrations between about 1 to 100 ng/mL are usually sufficient. Simple titration experiments routine in the art are used to determine the optimal concentration of a particular growth factor for a particular cell culture.

Cells of the invention that are proliferated in serum-free media should be grown in the presence of a substituted deoxynucleotide or deoxynucleoside compound such as, for example, halogenated-deoxynucleosides like bromodeoxyuridine (BrdU) or iododeoxyguanosine (IrdG), alkyl-substituted examples such as methyldeoxyguanosine, prior to transplantation into a host. The pre-transplant growth medium comprises the components of the long-term propagation media, but also contains substituted deoxynucleotide or deoxynucleoside compound concentrations between about 10 nanomolar and 100 micromolar, more preferably between about 2 and 50 micromolar, and more preferably about 10 micromolar. Pre-transplantation propagation can extend between about 1 and 10' days, more preferably between about 1 and 5 days and more preferably between about 2 and 3 days. Specially adapted MNSCs prepared according to the methods of the invention are conditioned or adapted to proliferate, migrate and differentiate properly when transplanted into host tissue such that, for example, a cognitive improvement can be seen in an animal with a neurological deficit.

Cellular preparations and pharmaceutical compositions of the MNSCs of the invention are also provided herein. Pharmaceutical compositions optimally comprise a therapeutically effective, amount of the MNSCs in admixture with a pharmaceutically or physiologically, acceptable formulations agent selected for suitability with the mode of administration. Acceptable formulation materials preferably about nontoxic to the specialty adapted MNSCs and th recipients at the dosages and concentrations employed.

The cellular preparations and pharmaceutical compositions of the invention may contain formulation materials for modifying, maintaining, or preserving, for example, pH, osmolarity, viscosity, clarity, color, isotonicity, odor, sterility, stability, rate of dissolution or release, adsorption, or penetration of the composition, as well as proliferation, migration and differentiation capacity of the specially adapted MNSCs of the invention. Suitable formulation materials include, but are not limited to, amino acids (such as glycine, glutamine, asparagine, arginine, or lysine), antimicrobial compounds, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See Remington's Pharmaceutical Sciences (18th Ed., A. R. Gennaro, ed., Mack Publishing Company 1990).

The primary vehicle or carrier in a pharmaceutical composition may be either aqueous or non-aqueous in nature. For example, a suitable vehicle or carrier for injection may be water, physiological saline solution, or artificial cerebrospinal fluid. Optimal pharmaceutical compositions will be determined by a skilled artisan depending upon, for example, the intended route of administration, delivery format, desired dosage and recipient tissue. See, e.g., Remington's Pharmaceutical Sciences, supra. Such compositions may influence the physical state, stability, and effectiveness of the NSC composition.

The invention provides methods of delivery and transplantation of the specially adapted MNSCs of the invention to ameliorate the effects of age, physical and biological trauma and degenerative disease on the brain or central nervous system of an animal, as well as other tissues such as, for example retinal tissue. It is well recognized in the art that transplantation of tissue into the CNS offers the potential for treatment of neurodegenerative disorders and CNS damage due to injury. Transplantation of new cells into the damaged CNS has the potential to repair damaged, circuitries and provide neurotransmitters thereby restoring neurological function. It is also recognized in the art that transplantation into other tissue, such as eye tissue, offers the potential for treatment of degenerative disorders and tissue damage due to injury. As disclosed herein, the invention provides methods, for generating MNSCs adapted for proliferation, migraton and differentiation in mammalian tissue when introduced thereto. The use of the MNSCs in the treatment of neurological disorders and CNS damage, as well as the use of NSCs in the treatment of other tissue damage or degeneration, can be demonstrated by the use of established animal models known in the art.

MNSCs of the invention can be administered to an animal with abnormal or degenerative symptoms obtained in any manner, including those obtained as a result of age, physical or biological trauma, or neurodegenerative disease and the like or animal models created by man using recombinant genetic techniques, such as transgenic and "gene knockout" animals.

Recipients of the MNSCs of the invention can be immunosuppressed, either through the use of immuno suppressive drugs such as cyclosporin, or through local immunosuppression strategies employing locally applied immunosuppressants, but such immunosuppression need not necessarily be a prerequisite in certain immunoprivileged tissues such as, for example, brain and eye tissues. In certain embodiments, the delivery method of the invention can cause less localized tissue damage to the site of cell damage or malfunction than existing methods of delivery, MNSCs of the invention can be prepared from the recipient's own tissue. In such instances, the progeny of the NSCs can be generated from dissociated or isolated tissue and proliferated in vitro using the methods described herein. Upon suitable expansion of cell numbers, the stem cells of the invention can be harvested, treated according to the methods of the invention and readied for administration into the recipient's affected tissue.

There are significant differences in the method of delivery to the brain of the MNSCs of the invention as compared to the prior art. One exemplary difference is as follows: the MNSCs of the invention are transplanted intraventricularly. Further, while the transplantation of one or more separate MNSCs is efficacious, the MNSCs of the invention are preferably transplanted in the form of clusters of two or more cells via a surgical procedure or injection using a syringe large enough to leave the clusters substantially intact. The results disclosed in the Examples below indicate that ventricular delivery of the MNSCs of the invention in the form of a cluster of two or more cells can result in migration to the area of damage in the brain and proper neuronal differentiation. Another benefit of intraventricular injection is less tissue destruction, resulting in less localized recruitment of immune cells by the host. This is evidenced by the lack of ventricular distortion, tumor formation, and increased host astrocyte staining without any immunosuppression.

The method of delivery of the MNSCs of the invention to the brain can be essentially duplicated for other immunoprivileged tissue such as, for example, the eye. Delivery of one or a plurality of separate or two or more MNSCs of the invention in the form of a cluster via injection using a syringe large enough to leave any cluster or two or more cells that is present substantially intact can result in migration to the area of damage in the eye and proper tissue-specific differentiation.

There are examples in the art of intra-tissue injection (brain) of dissociated and partially differentiated NSCs (see, e.g., Benninger et al., 2000, *Brain Pathol.* 10: 330-341; Blakemore et al., 2000, *Cell Transplant.* 9: 289-294; Rosser et al., 2000, *Eur. J. Neurosci.* 12: 2405-2413; Rubio et al., 2000, *Mol. Cell. Neurosci.* 16: 1-13). Further, the dissociation of NSC clusters is known to cause immediate senescence of NSCs and increase the vulnerability of NSCs in culture. See, e.g., Svendsen et al., 1998, *J. Neurosci. Methods* 85: 141-152. Some aspects of the instant invention preferentially employ injection of clusters of two or more cells, but the specially adapted cells of the invention appear to migrate and differentiate appropriately when transplanted in non-cluster from as well. As provided by this invention, intraventricular transplantation provides an alternative route to the site-specific injection disclosed in the prior art. Using intraventricular transplantation, grafted cells can gain access to various structures by the flow of CSF, and transplantation of more developmentally potent cells of the invention in cluster form can act to prevent premature differentiation at inappropriate anatomical sites in the brain and central nervous system. Regarding the eye, intraocular administration of clusters of two or more cells, for example into the vitreous fluid, allows the more developmentally potent cells of the invention to migrate to the area of degeneration or injury and differentiate appropriately Delivery of MNSCs of the invention into other, non-immunoprivileged tissues can also be carried out, particularly when the MNSCs are autologous to the recipient, including systemically (e.g., intravenously).

Figure 2:
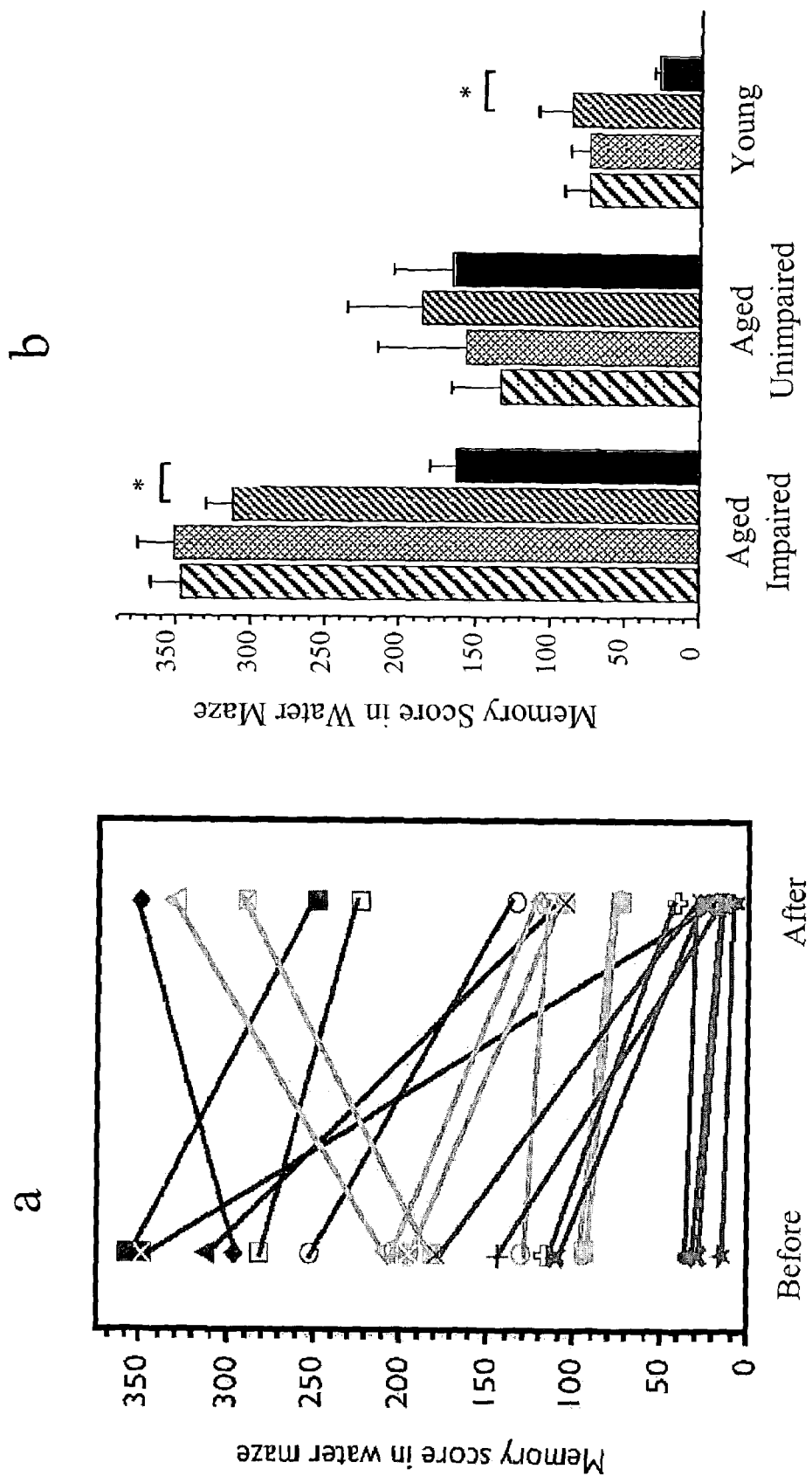
FIG. 2 shows the effect of NSC transplantation on memory score in the Morris water maze test. (a) Individual memory score before and after transplantation shows improvement in the majority of the animals. Blue: Aged memory impaired animals, Green: Aged memory unimpaired animals, Red: Matured animals. (b) Mean of memory score in each animal group before (narrow striped bar) and after (black bar) MNSCs transplantation shows a significant improvement in aged memory impaired and young animals. The animals that received vehicle injection do not show significant difference in memory score between before (wide striped bar) and after (hatched) the injection.

Functional integration of the graft into the host's neural tissue can be assessed by examining the effectiveness of grafts on restoring various functions, including but not limited to tests for endocrine, motor, cognitive and sensory functions. Useful motor tests include tests that quantitate rotational movement away from the degenerated side of the brain, and tests that quantitate slowness of movement, balance, coordination, akinesia or lack of movement, rigidity and tremors. Cognitive tests include tests of the ability to perform everyday tasks, as well as various memory tests, including maze performance such as the Morris water maze performance. For example, using the cells and methods of the invention, MNSCs injected into the ventricle of 24-month-old rats after in vitro expansion displayed extensive and positional incorporation into the aged host brain with improvement of cognitive score (FIG. 2), as assessed by the Morris water maze after 4 weeks of the transplantation. Results of the experiments disclosed herein indicate that the aged brain is capable of providing the necessary environment for MNSCs of the invention to retain their multipotent status and demonstrate the potential for neuroreplacement therapies in age associated neurodegenerative disease.

Figure 3:
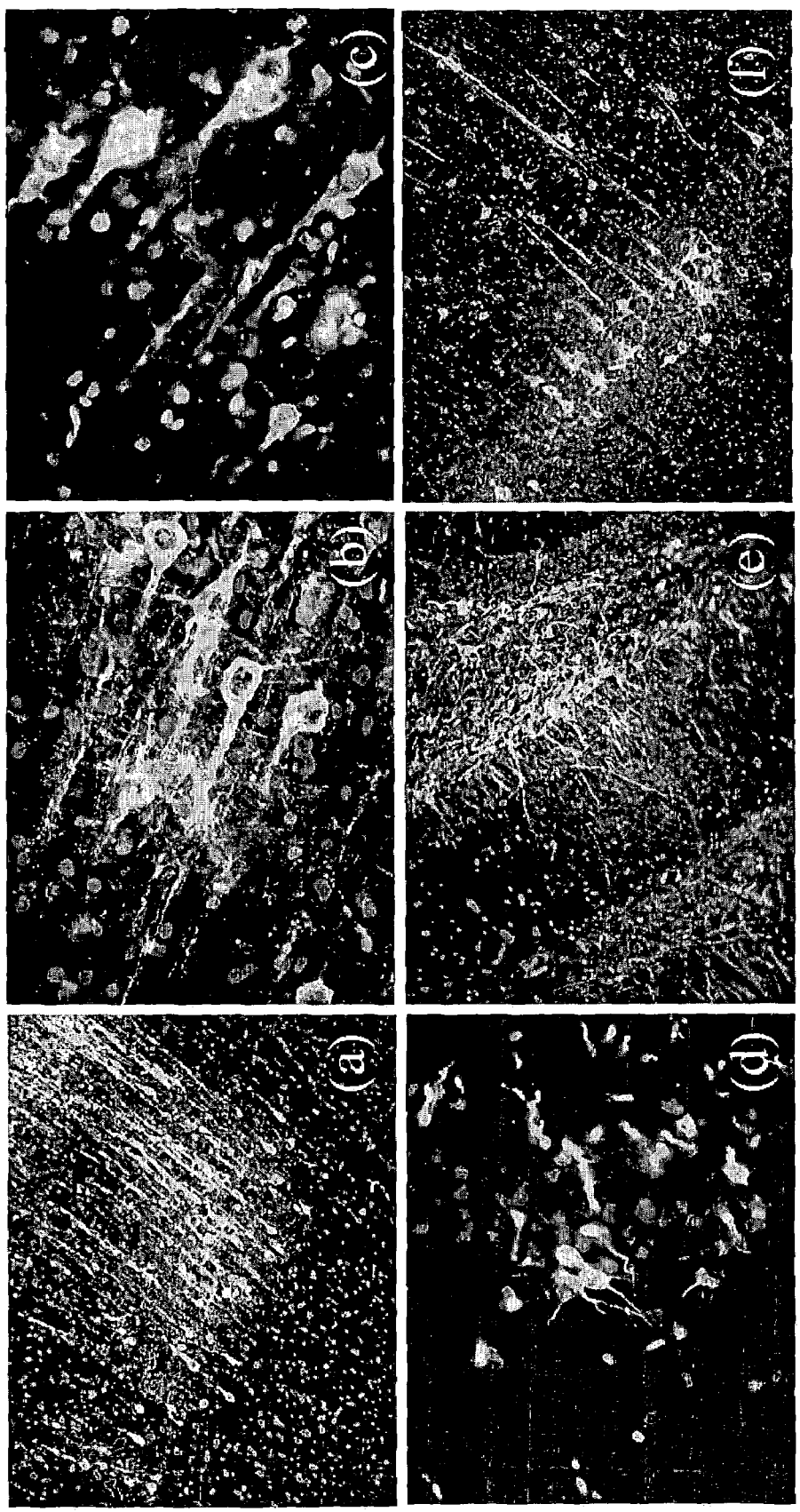
FIG. 3 shows typical fluorescent immunohistochemical photomicrographs of aged rat brain 30 days after NSCs transplantation. bIII-tubulin and GFAP immunoreactivity were used as markers for neuron and glia, respectively. (a) MNSCs of the invention migrated into the cortex and differentiated into neurons as indicated by the bIII-tubulin positive cells (green), which have morphologies typical of pyramidal cells in layer IV and V, of the parietal cortex. Apical dendrites were pointed towards to the edge of the cortex. Since the NSCs were pre-treated with BrdU, the transplanted cells have BrdU positive nuclei (red). Contrarily, the host cell's nuclei are counter stained with DAPI (blue). Many cells having BrdU positive nuclei are observed with bIII-tubulin immunoreactivity in layer II and without bIII-tubulin immunoreactivity in layer III. (b, c) Higher magnification of the parietal cortex in cortex layer IV: All the bIII-tubulin immunoreactive (green) positive cells show BrdU (red) positive nuclei while many other host cell's nuclei are stained with only DAPI (blue). NSCs tend to have larger nuclei than host cells. (d) NSCs migrated into the hippocampus and differentiated into bIII-tubulin positive cells. (green), in CA1 pyramidal cell layer. These bIII-tubuln positive cells have BrdU positive nuclei (red), indicating that these cells originated from transplanted cells. In contrast, host cell nuclei counter stained with DAPI (blue) are not bIII-tubulin positive. (e) In the dentate gyrus many fibers were bIII-tubulin positive in addition to the bIII-tubulin positive cells (green) and GFAP positive sells (red), (f) bIII-tubulin positive cells (green) and GFAP positive cells (red) were found in layer IV and layer III, respectively. Such a layer of astrocytes were not observed in normal rats without NSC transplantation.

Functional integration of the graft into the host's other tissue can be assessed by examining the effectiveness of grafts on restoring various functions specific to the injured or degenerated tissue, for example improvement in sight for transplantation of stem cells of the invention to the eye. Regarding the eye, using the cells and methods of the invention, MNSCs of the invention injected into the vitreous cavity of rat eyes after in vitro expansion displayed extensive and positional incorporation into the host eye tissue (FIG. 3) 4 weeks post-transplantation. Results of the experiments disclosed herein indicate that the eye, as with the brain, is capable of providing the necessary environment for the MNSCs of the invention to differentiate in a tissue-specific manner, and thus demonstrate the-potential for replacement therapies in injury or degeneration-associated tissue damage.

Without being restricted to any particular theory for the mechanism of action of the cells and methods of the invention, there are at least two explanations for the beneficial effects of transplantation of MNSC of the invention to cognitive function of the, host brain as well as the beneficial effects of these MNSCs in other tissues. One is replacement or augmentation. Neural circuits can be replaced or augmented by the MNSC-derived neurons. In other tissues, cells and cell structures can also be replaced or augmented by MNSC-derived cells appropriate for that tissue. An alternative explanation is the trophic action of factors released from the transplanted MNSCs. Morphological analysis of rat brains transplanted with the MNSCs as disclosed herein showed extensive incorporation of the MNSCs and massive growth of neural fibers in the host brain area related to spatial memory task (FIGS. 3 and 4); however, the MNSCs may still migrate toward the damaged neurons and rescue them by the production of neurotrophic factors. Synergy between these two explanations may also exist.

As assessed by the Morris water maze test, improvement in spatial memory of animals transplanted with the specially adapted MNSCs was accompanied by incorporation of the MNSCs into the brain areas known to be related to spatial memory. The post-transplant morphology of rat brain tissue indicates that functional association of the transplanted cells to the host brain occurs. Immunohistochemical analysis revealed that the bIII-tubulin-positive donor-derived cells found in the cerebral cortex are characterized by possessing dendrites pointing to the edge of the cortex; whereas, in the hippocampus, donor-derived neurons exhibited morphologies with multiple processes and branches. These differential morphologies of the transplanted MNSCs in different brain regions indicate that site-specific differentiation of the MNSCs occurs according to various factors present in each brain region.

Strong astrocyte staining was also found in the frontal cortex layer 3 and CA2 region of hippocampus in transplanted rat brains, areas where astrocytes are not normally present in the animal. The migration of the MNSCs of the invention to the CA2 is of particular interest because CA2 pyramidal neurons highly express bFGF, and the expression of bFGF is up-regulated by entorhinal cortex lesions (see, e.g., Eckenstein et al., 1994, *Biochem. Pharmacol.* 47: 103-110; Gonzalez et al., 1995, *Brain Res.* 701: 201-226; Williams et al., 1996, *J. Comp. Neurol.* 370. 147-158). CA2 pyramidal neurons in the host brain can express bFGF as a response to a reduction of synaptic transmission, an event that can occur during aging. Subsequently, this expressed bFGF can act as a signal for the transplanted MNSCs to respond, migrate or proliferate under the influence of bFGF produced in the host brain after the transplantation.

The regions rich in astrocyte staining transplanted rat brains are the same regions where extensively stained neural fibers were identified (FIGS. 3a, 3d and 3e). During development, glial cells have many complex functions, such as neural and axonal guidance and production of trophic factors (see, e.g. Pundt et al., 1995, *Brain Res.* 695: 25-36). This overlapping distribution of glial and neural fibers strongly suggests that this interaction plays a pivotal role in the survival, migration, and differentiation of transplanted MNSCs.

Immunohistochemistry of transplanted rat brains reveals a symmetrical distribution of neurons and astrocytes at both sides of the host brain, indicating that the progeny of these specially adapted MNSCs can migrate. Although astrocytes have been shown to migrate over long distances following transplantation (see, e.g., Blakemore et al., 1991, *Trends Neurosci.* 14: 323-327; Hatton et al., 1992, *Glia* 5: 251-258; Lundberg et al., 1996, *Exp. Neurol.* 139: 39-53), there is experimental evidence showing that neurons do not migrate as widely as glial cells (see, e.g., Fricker et al., 1999, *J. Neurosci.* 19: 5990-6005). As disclosed herein, neural precursors derived from the MNSCs of the invention possess similar migratory capacity to astrocyte precursors.

Information pertaining to neural stem cells is presented, followed by information pertaining to retinal stem cells. One of skill in the art will readily recognize the methods of the invention are not limited to these three types of stem cells and instead extend to cover all cell types not yet terminally differentiated.

Neural-Related

Due to the generally low proliferation rate of mammalian NSCs there is a correlation between advancing age and impaired brain function even in the absence of specific neurodegenerative disease or physical or biological brain trauma. The invention provides methods for counteracting impaired brain function due to advancing age through the addition of specially adapted MNSCs capable of proliferation, migration and differentiation in mammalian brain when introduced thereto.

Physical trauma and biological trauma are additional causes of impaired or improper brain function. The term "physical trauma" denotes brain cell damage due to external sources such as blunt head trauma, severe concussion and the like. Such physical trauma can be localized or general depending on the source and severity of the trauma. The term "biological trauma" denotes any acute brain injury that has its origin in a biological process, for example, stroke, aneurysm, epilepsy, brain tumor, hypoxia and the like.

Another source of impaired or improper brain function is neurodegenerative disease. In recent years neurodegenerative disease has become an important concern due to an expanding elderly population that is at greatest risk for these disorders. Neurodegenerative diseases include, but are not limited Alzheimer's disease, amyotrophic lateral sclerosis (ALS), Parkinson's disease, Pick's disease, Huntington's disease, progressive supranuclear palsy, corticobasal degeneration, Parkinson-ALS-dementia complex, Gerstmann-Straussler-Scheinker syndrome, Hallervorden-Spatz disease, Kufs' disease, Wilson's disease, multiple sclerosis (MS), late-onset metachromatic leukodystrophy and adrenoleukodystrophy. The effects of these diseases can be counteracted by: administration of the MNSCs of the invention.

There is a variety of organic brain diseases that impairs motor or cognitive function. Degeneration in the basal ganglia can lead to diseases with cognitive and motor symptoms, depending on the exact location of the degeneration. Motor deficits are a common result of degeneration in the basal ganglia. Huntington's Chorea is associated with the degeneration of neurons in the striatum, which leads to involuntary jerking movements in the host. Degeneration of a small region called the subthalamic nucleus is associated with violent flinging movements of the extremities in a condition called ballismus, while degeneration in the putamen and globus pallidus is associated with a condition of slow writhing movements or athetosis. In Parkinson's disease, degeneration is seen in another area of the basal ganglia, the substantia nigra par compacta. This area normally sends dopaminergic connections to the dorsal striatum, which are important in regulating movement. Therapy for Parkinson's disease has centered upon restoring dopaminergic activity to this circuit, which can be accomplished by transplantation of neural stem cells to this region of the brain according to the instant invention.

In Alzheimer's disease, another neurodegenerative disease, there is substantial cellular degeneration of the forebrain and cerebral cortex. Further, a localized area of the basal ganglia, the nucleus basalis of Meynert, appears to be selectively degenerated. This nucleus normally sends cholinergic projections to, the cerebral cortex, which are thought to participate in cognitive functions including memory.

Although adult stem cells continue to possess some multipotency, cell types produced from adult stem cells are limited by their tissue-specific character. For example, human NSCs spontaneously differentiate into brain cells under basal media conditions, but retinal or mesenchymal stem cells cannot spontaneously differentiate into neural cells without the addition of certain factors (see concurrent application entitled "Novel Mammalian Multipotent Stem Cells And Compositions, Methods Of Preparation And Methods Of Administration Thereof"). These results indicate that each stem cell contains specific information that permits it to become a special type of cell, i.e., they are partially committed to become a particular type of cell in a tissue-specific manner. To overcome this barrier of stem cell lineage, alterations to the cells and their environment are necessary. However, the exact regulation mechanisms of tissue-specific stem cell fate decisions remain unclear. This gap in the knowledge base poses an important problem, because although NSCs can be isolated and proliferated in culture, they cannot naturally differentiate into non-neural-lineage cells. Further, untreated, unaltered NSCs have not, hitherto, been known to migrate and differentiate properly such that a neurological or corporal deficit could be remedied as shown in Example 1 below.

Retinal Related

Retinal degenerative diseases, including macular degeneration, are major causes of blindness. Despite investigations into gene therapy, growth/survival factor injections and vitamin treatments, no effective vision-restoring treatments are currently available. Visual impairment caused by the degeneration of photoreceptors or neural cells has been considered incurable because of a long-held "truism"; neurons do not regenerate during adulthood. However, this statement has been challenged and we have found new evidence that these cells do indeed have the potential to be renewed after maturation, thus opening a door for the development of novel therapies to treat visual impairment by retinal regeneration B using stem cell transplantation.

The capacity for retinal regeneration in cold-blooded vertebrates has long been recognized. Fish and amphibians continue to make new retinal neurons through a population of retinal stem cells residing at the peripheral margin of the retina, the so-called "ciliary marginal zone." Recent studies have provided evidence that birds and adult mammals also possess a zone of cells at the retinal margin analogous to the ciliary marginal zone of cold-blooded vertebrates. These retinal stem cells are reported not only to generate photoreceptor and other retinal cells in vitro, but also to differentiate into retinal cells following transplantation into the retinal area. Although these results indicate the possibility of retinal regeneration therapy, since the number of retinal stem cells is limited, we must locate an alternative source of stem cells for use in clinical applications.

Neural stem cells have been isolated from embryonic and adult mammalian brains and have been propagated in vitro in a variety of culture systems. Using a serum-free unsupplemented media condition, NSCs spontaneously differentiated into bIII-tubulin-, glial fibrillary acidic protein (GFAP)-, and O4-immunopositive cells, markers for neurons, astrocytes, and oligodendrocytes, respectively. As described in the examples below, NSCs treated according to methods of the invention migrate and differentiate into neurons and glia after transplantation into the brains of 24-month-old rats and significantly improved the cognitive functions of these animals. This result led us to consider that MNSCs of the invention could represent transplantable material to produce a retinal stem cell alternative.

There are variety of factors involved in the development of retinal tissue that regulate the proliferation and differentiation of retinal cells. Transforming growth factor beta 3 (TGF-b3) is thought to regulate cell proliferation during development and influence the commitment or the differentiation, or both, of neural progenitor cells to retinal fates. Treatment of embryonic day-18 rat retinal cultures with TGF-b-like protein activin A, causes the progenitor cells in these cultures to exit the cell cycle and differentiate into rod photoreceptors, indicating that the TGF family is an important regulator of photoreceptor differentiation in the developing retina. Treatment of neural stem cells or MNSCs prepared according to the invention before or concurrently with TGF-b3, CNTF, IGF-1, or combinations of two or more thereof, can induce their adoption of a retinal differentiation path in vitro. Further, treatment of untreated neural stem cells or MNSCs of the invention with one or more of the factors before or concurrent with transplantation can induce their adoption of a retinal differentiation path in vivo. "Retinal differentiation" and "retinal cell" as used herein, refers to the various cell types found in eye tissue, inter alia, chorid, Buchs and retinal pigment epithelium cells, rod and cone photoreceptor cells, horizontal cells, bipolar neurons, amacrine, ganglion and optic nerve cells. These non-limiting, exemplary cell types found in eye tissue are collectively referred to as retinal cells.

Previous transplantation studies of NSCs into retinal tissue with rd mice (a model of retinitis pigmentosa); mechanical lesions, transient ischemia and normal retina have revealed that donor cells migrate into the retinal area and differentiate into neurons and glia, but they do not show any retinal cell markers. These results indicate that NSCs are already committed to become neural tissue, and that this commitment is not mutable solely by transplantation into the retina. Thus, to differentiate NSCs into retinal cells, alteration of their epigenetic information before retinal transplantation appears necessary, something accomplished by the methods of the invention. Thus, using the methods of the invention, MNSCs can be used as alternatives to retinal stem cells to repair ocular tissue damage or promote tissue regeneration.

The inventive methods use BrdU and other substituted deoxynucleotide or deoxynucleoside compounds to change the cell fate decisions of NSCs to those of the specially adapted MNSCs described herein. Such an invention is important in the neuroreplacement therapy field because it demonstrates cognitive improvement due to transplantation of substituted deoxynucleotide or deoxynucleoside compound-treated NSCs. Stem cell can be purchased or isolated from the patient, expanded in vitro, genetically modified and transplanted back to the same patient. Since neural stem cells of the invention can be differentiated to most peripheral tissue cells, the invention is not only useful to neuroreplacement but to other kinds of tissue regeneration or replacement as well. In addition, in the case of autologous transplantation, there are no ethical barriers or immunorejection issues with which to contend.

There are a variety of neurological and corporal deficits that can be addressed using the cells of the invention.

Neurological Deficits" Amenable to Treatment

Because the invention relates to the discovery that multipotent neural precursor cells can be stimulated to divide and migrate through the brain, it can be used to treat neurological deficits caused by a wide variety of diseases, disorders, and injuries. These insults include, but are not limited to, the following (others of skill in the art may categorize differently the diseases and disorders listed below; however categorized, the neurological deficits with which they are associated are: amenable to treatment according to the methods of the present invention).

Degenerative Diseases

Degenerative diseases that can be treated according to the methods of the invention include Alzheimer's disease (AD), Parkinson's disease (PD), Huntington's disease (HD), Pick's disease, progressive supranuclear palsy (PSP), striatonigral degeneration, cortico-basal degeneration, childhood disintegrative disorder, olivopontocerebellar atrophy (OPCA; including a heritable form), Leigh's disease, infantile necrotizing encephalomyelopathy, Hunter's disease, mucopolysaccharidosis, various leukodystrophies (such as Krabbe's disease, Pelizaeus-Merzbacher disease, and the like), amaurotic (familial) idiocy, Kufs disease, Spielmayer-Vogt disease, Tay Sachs disease, Batten disease, Jansky-Bielschowsky disease, Reye's disease, cerebral ataxia, chronic alcoholism, beriberi, Hallervorden-Spatz syndrome, and cerebellar degeneration.

Traumatic and Neurotoxic Injuries to the Central Nervous System

Traumatic and neurotoxic injuries that can be treated according to the methods of the invention include gunshot wounds, injuries caused by blunt force, injuries caused by penetration injuries (e.g., stab wounds), injuries caused in the course of a surgical procedure (e.g., to remove a tumor or abscess from the CNS or to treat epilepsy), poisoning (e.g., with MPTP or carbon monoxide), shaken-baby syndrome, adverse reactions to medication (including idiosyncratic reactions), drug overdose (e.g., from amphetamines), and post-traumatic encephalopathy.

Ischemia

Any disruption of blood flow or oxygen delivery to the nervous system can injure or kill cells, including neurons and glial cells, therein. These injuries can be treated according to the methods of the present invention and include injuries caused by a stroke (including a global stroke (as may result from cardiac arrest, arrhythmia, or myocardial infarction) or a focal stroke (as may result from a thrombus, embolus, hemorrhage, or other arteral blockage)), anoxia, hypoxia, partial drowning, myoclonus, severe smoke inhalation, dystonias (including heritable dystonias), and acquired hydrocephalus.

Developmental Disorders

Developmental disorders that can be treated according to the methods of the invention include schizophrema, certain forms of severe mental retardation, cerebral palsy (whether caused by infection, anoxia, premature birth, blood type incompatbility: etc. and whether manifest as blindness, deafness, retardation, motor skill deficit, etc.), congenital hydrocephalus, metabolic disorders affecting the CNS, severe autism, Down Syndrome, LHRH/hypothalamic disorder, and spina bifida.

Disorders Affecting Vision

Disorders affecting vision, particularly those caused by the loss or failure of retinal cells, can be treated according to the methods and cells of the invention. These disorders include, for example, diabetic retinopathy, serious retinal detachment, retinal damage associated with glaucoma, traumatic injury to the retina, retinal vascular occlusion, macular degeneration (wet or dry), post-surgical healing, tumor, heritable retinal dystrophies, optic nerve atrophy, and other retinal degenerative diseases. Cells targeted for repair utilizing cells and methods of the invention include, for example, choroids, Buchs, retinal pigment epithelial (RPE), rods, cones, horizontal cells, bipolar neurons, amacrine, ganglion, and optic nerve.

Injuries and Diseases of the Spinal Cord

Injuries to or diseases affecting the spinal cord can also be treated according to the methods of the invention. Such injuries or diseases include post-polio syndrome, amyotiophic lateral sclerosis, nonspecified spinal degeneration, traumatic injury (such as those caused by automobile or sporting accidents), including any injury that crushes, partially severs, completely severs, or otherwise adversely affects the function of cells in the spinal cord), injuries caused by surgery to the spinal cord (e.g., to remove a tumor), anterior horn cell disease, and paralytic diseases.

Demyelinating or Autoimmune Disorders

Neurological deficits caused by demyelination or an autoimmune response can be treated according to the methods of the invention. Such deficits can be caused by multiple sclerosis, possibly lupus, and others.

Infectious or Inflammatory Diseases

Neurological deficits caused by an infection or inflammatory disease can be treated according to the methods of the invention. Infections or inflammatory diseases that can cause treatable deficits include Creutzfeldt-Jacob disease and other slow virus infectious diseases, AIDS encephalopathy, post-encephalitic Parkinsonism, viral encephalitis, bacterial meningitis and meningitis caused by other organisms, phlebitis and thrombophlebitis of intracranial venous sinuses, syphilitic Parkinsonism, and tuberculosis of the CNS.

Miscellaneous

Those of ordinary skill in the art are well able to recognize neurological deficits, regardless of their cause, and to apply the methods of the present invention to treat patients who have such deficits. In addition to the conditions listed above, which are amenable to treatment with the methods described herein, neurological deficits can be caused by Lesch-Nyhan syndrome, myasthenia gravis, various dementias, numerous parasitic diseases, epilepsy, and the like. Further, alleviation of age-related memory loss is an object of the invention. The methods of the invention can be readily applied to alleviate neurological deficits caused by these and other diseases, disorders, or injuries.

"Corporal Deficits" Amenable to Treatment

The invention also relates to the amelioration of corporal deficits utilizing multipotent precursor cells stimulated to divide, migrate through damaged tissue and differentiate in a tissue-specific manner. Cells according to the invention can be used to treat corporal deficits caused by a wide variety of diseases, disorders, and injuries, the result of which is trauma, malfunction, degeneration or loss of muscle such as, for example, cardiac muscle due to myocardial infarction. Other examples include malfunction, degeneration or loss of other cells and tissues apart from those discussed in the neurological deficit section above such as, for example, internal organs. For example, liver function can be adversely affected by, among other things, disease (e.g., cirrhosis or hepatitis), trauma or age. Other exemplary internal organs amenable to treatment utilizing the embodiments of the invention include heart, pancreas, kidney, stomach, and lung. Corporal deficits also comprise malfunction, degeneration or loss of skeletal assets such as, for example, vertebrae.

An advantage of the cells of the invention is that they can be genetically engineered according to routine procedures known in the art (See, e.g., Sambrook et al., 2001, MOLECULAR CLONING: A LABORATORY MANUAL. 3rd ed., Cold Spring Harbor Laboratory. Press: N.Y.). In certain embodiments, constructs; encoding proteins of interest can be provided to the cells. In other embodiments, constructs that inhibit expression of desired proteins can be provided (such as, for example, ribozymes and antisense molecules). In further embodiments, drug resistance genes and markers, or detectable markers such as GFP can be provided. Preferably, the marker and other genes are operably and genetically linked to gene expression regulatory elements (including but not limited to promoters and enhancers) that are operable in a terminally differentiated cell derived from the MNSCs of the invention or in the undifferentiated MNSCs of the invention or both.

The following examples are presented in order to more fully illustrate the preferred embodiments of the invention. They should in no way be construed, however, as limiting the scope of the invention, as defined by the appended claims.

EXAMPLES

Example 1

Improvement of Cognitive Function in Aged Rat by the Transplantation of MNSCs of the Invention Human NSCs do not require any exogenous factors for differentiation and survived: more than three weeks in basal media without the addition of any factor to support the survival (Qu et al. 2001, *Neuroreport* 12: 1127-32). Nevertheless, NSCs have heretofore not been successfully transplanted such that proper migration and differentiation and cognitive improvement has been observed. Thus, it appears that human NSCs produce factors to differentiate and support themselves, which suggested that these cells could be transplanted into aged animals after treatment according to the methods of the invention.

Human NSCs, expanded without differentiation under the influence of mitogenic factors in supplemented serum-free media and pre-treated by the incorporation of broniodeoxyuridine (BrdU) into the nuclear DNA, were injected into the lateral ventricle of mature (6-month-old) and aged (24-month-old rats. Human NSCs prepared according the methods of the invention survived 30 days after xenotransplantation into aged rat brain while retaining both multipotency and migratory capacity, and also improved cognitive function in 24-month-old rats. Cognitive function of the animals was assessed by the Morris water maze both before and four weeks after the transplantation of human MNSCs of the invention. Before human NSC transplantation, some aged animals (aged memory unimpaired animals) cognitively functioned in the range of mature animals, while others (aged memory impaired animals) functioned entirely out of the cognitive range of the mature animals. After transplantation of the BrdU-treated human NSCs, most aged animals had cognitive function in the range of the mature animals. Strikingly, one of the aged memory-impaired animals showed dramatic improvement in its behavior, functioning even better than the mature animals (FIG. 2a). Statistical analysis showed that cognitive function was significantly improved in both mature and aged memory-impaired animals but not in aged memory-unimpaired animals after BrdU-treated human NSC transplantation (FIG. 2b), which may be due to the physical limitations of the aged animals. The performance of three of the aged animals deteriorated in the water maze after transplantation of treated human NSCs. It is possible that the physical strength of these animals deteriorated during the experimental period.

These behavioral results indicate the beneficial effects of the transplantation of BrdU-treated human NSCs into the host brain. After the second water maze task, postmortem brains were further analyzed by immunohistochemistry for human bIII-tubulin and human GFAP, markers for neurons and astrocytes respectively. There was no sign of ventricular distortion, no evidence of tumor formation, and no strong host anti-graft immunoreactivity was observed as revealed by weak host Xastrocyte staining. Intensely and extensively stained with bIII-tubulin, neurons with BrdU-positive nuclei were found in bilateral singular and parietal cortexes (FIG. 3a-c) and hippocampus (FIG. 3d,e). The bIII-tubulin-positive neurons found in the cerebral cortex were typified by a dendrite pointing to the edge of the cortex. In the hippocampus, donor-derived neurons exhibited multiple morphologies, varying in cellular size and shape, and one or more processes and branching.

Generally, GFAP-positive astrocytes were localized near the area where neural cells were found. On further analysis (overlapping images of their distributions), donor-derived astrocytes were found to co-localize with neural fibers in the cortex (FIG. 3f). These astrocytes were larger than the host glia, with cell bodies 8-10 microns in diameter and thick processes. Some of these astrocytes had a unilateral morphology (asymmetric), and the immunostaining formed a thin ring around the nucleus, while the majority of the processes were formed on the other side. Most cells appeared a symmetrical with processes forming from all sides. The absence of this type of cell in normal animal without the transplantation of treated human NSCs was confirmed using immunohistochemistry for rat astrocytes host astrocytes had small cell bodies with multiple delicate processes, and were distributed throughout the brain mainly in white matter and around the edges of the brain.

These results demonstrated that transplanted cells of the invention migrated in rat brain and differentiated into appropriate cell types. The concomitant improvement in cognitive function indicated that transplanted MNSCs of the invention were functionally integrated into the recipient brains.

The following methods were used in this and several of the following examples:

The Morris Water Maze: The Morris water maze consists of a large circular tank (diameter, 183 cm; wall height, 58 cm), filled with water (27° C.) and pacified by the addition of powdered milk: (0.9 kg). Beneath the water surface (1 cm) near the center of one of the four quadrants of a maze clear escape platform (height, 34.5 cm) is positioned. The rats receive three training trials per day for seven consecutive days, using a 60 sec inter-trial interval. A training trial consists of placing the animal in the water for 90 seconds or until the swimming rat successfully locates the platform. If the rat fails to find the platform within the 90 seconds, the animal is gently guided to the platform. For spatial learning assessment, the platform's location remains constant in one quadrant of the maze, but the starting position for each trial is varied. Every sixth trial is a probe trial, during which the platform is retracted to the bottom of the pool for 30 sec and then raised and made available for escape. The training trials assess the acquisition and day-to-day retention of the spatial task while the probe tests are used to: assess search strategy. At the completion of a spatial learning assessment, one session: with six trials of cue training is performed. Rats are trained to escape to a visible black platform that is raised 2 cm above the surface of the water. The location of the platform is varied from trial to trial to assess sensor motor and motivational functioning independent of spatial learning ability. Each rat is given 30 seconds to reach the platform and is allowed to remain there briefly before the 30 second inter-trial interval. Accuracy of performance is assessed using a learning index score computed from the probe trials. The learning index is a derived measure from average proximity (cumulative search error divided by the length of the probe trial) on the second, third, and fourth interpolated probe trials. Scores from these trials are weighted and summed to provide an overall measure of spatial learning ability. Lower scores on the index indicate a more accurate search near the target location; higher scores indicate a more random search and poor learning.

Cell migration and differentiation: In order to investigate differentiation and/or migration of cells of the invention in the brain, MNSCs were transplanted into rodent brain. The animals were anesthetized with 50 mg/kg pentobarbital (i.p.) and mounted in a stereotaxic apparatus (David Kopf). Approximately $1 \times 10^4$ to $1 \times 10^5$ cells in 5 µl phosphate-buffered saline were injected into the ventricle using a microsyringe attached to the stereotaxic apparatus. After removing the hair from the surgical site using electric razor, an iodine swab was be applied to the area and a 0.5 cm surgical incision was made caudal to rostral in the skin at the surface of the cranium. The ventricle was stereotaxically localized using the following exemplary coordinates: AP=−0.58 mm from bregma, ML=+1 mm, and 2.4 mm below dura (for mouse): AP=−1.4 mm from bregma, ML=+3.3 mm, and 4.5 mm below dura (for rat). A 0.4-mm hole was made in the cranium by careful drilling. The cells of the invention were injected into the ventricle using a microsyringe. The injection was delivered over a period of five minutes and the needle was left in place for an additional two minutes following the injection. After the injection, the surgically incised skin was closed by Michel suture clip (2.5× 1.75 mm). Ten days post-surgery, proper healing of the incision site was observed, and the Michel sutures were removed.

The existence and location of the cells of the invention after administration in rat brain were analyzed as follows. At 30 days post-transplantation, the rats were sacrificed by an overdose of sodium pentobarbital (70 mg/kg, i.p.) and perfused with phosphate buffered saline (PBS) followed by 4% paraformaldehyde. Brains were removed and incubated overnight in 4% paraformaldehyde fixative containing 20% sucrose. The brains were sliced into 20 micron coronal sections using a cryomicrotome. The sections were washed briefly in PBS and pretreated with 1M HCl for 30 minutes at room temperature and neutralized with sodium borate (0.1 M, pH 8.0) for 30 minutes in order to increase the accessibility of an anti-BrdU antibody to BrdU incorporated in the cell nuclei. After rinsing with PBS, sections were transferred to a solution containing 0.25% Triton X-100 in PBS (PBST) for 30 minutes. The sections were then blocked by incubation in PBST containing 3% donkey normal serum for 1 hour, followed by incubating the sections overnight at 48° C. with sheep anti-BrdU (1:1000; Jackson IR Laboratories, Inc. West Grove, Pa.) or mouse ariti-BrdU (1:200; DSHB, Iowa City, Iowa) diluted in PBST. After rinsing the sections in PBS, donkey anti-mouse or donkey anti-sheep conjugated to rhodamine IgG (Jackson IR Laboratories, Inc.) was added at a 1:200 dilution in PBST and the sections further incubated for 2 hours at room temperature in the dark.

The transplanted cells of the invention, with BrdU:immunopositive nuclei, were stained for human bIII-tubulin and human glial filament protein (GFAP). The sections were then washed with PBS and incubated with mouse IgG2b monoclonal anti-human bIII-tubulin, clone SDL3D10 (1:500, Sigma), goat antihuman. GFAP, N-terminal human affinity purified;: (1:200, Research Diagnostics Inc., Flander, N.J.) or mouse IgG1 monoclonal anti-GFAP, clone G-A-5 (1:500, Sigma), respectively, overnight at 48° C. in the dark. After brief washing with PBS to remove excess primary antibody, the location of primary antibody binding was then determined using FITC-conjugated (Jackson IR Laboratories, Inc.) secondary: antibody (donkey anti-mouse (1:200) or donkey anti-goat IgG (H+L; 1:200), respectively) by incubating the sections for 2 hours at room temperature in the dark.

The sections were then washed with PBS thoroughly before mounting to glass slides. The mounted sections were covered with Vectashield using 4',6-diamidine-2-phenylindole•2HCl (DAPI, Vector Laboratories, Inc., Burlingame, Calif.) for fluorescent microscopic observation. Microscopic images were taken by using an Axiocam digital camera mounted on the Axioscope 2 with Axiovision software (Zeiss).

Figure 4:
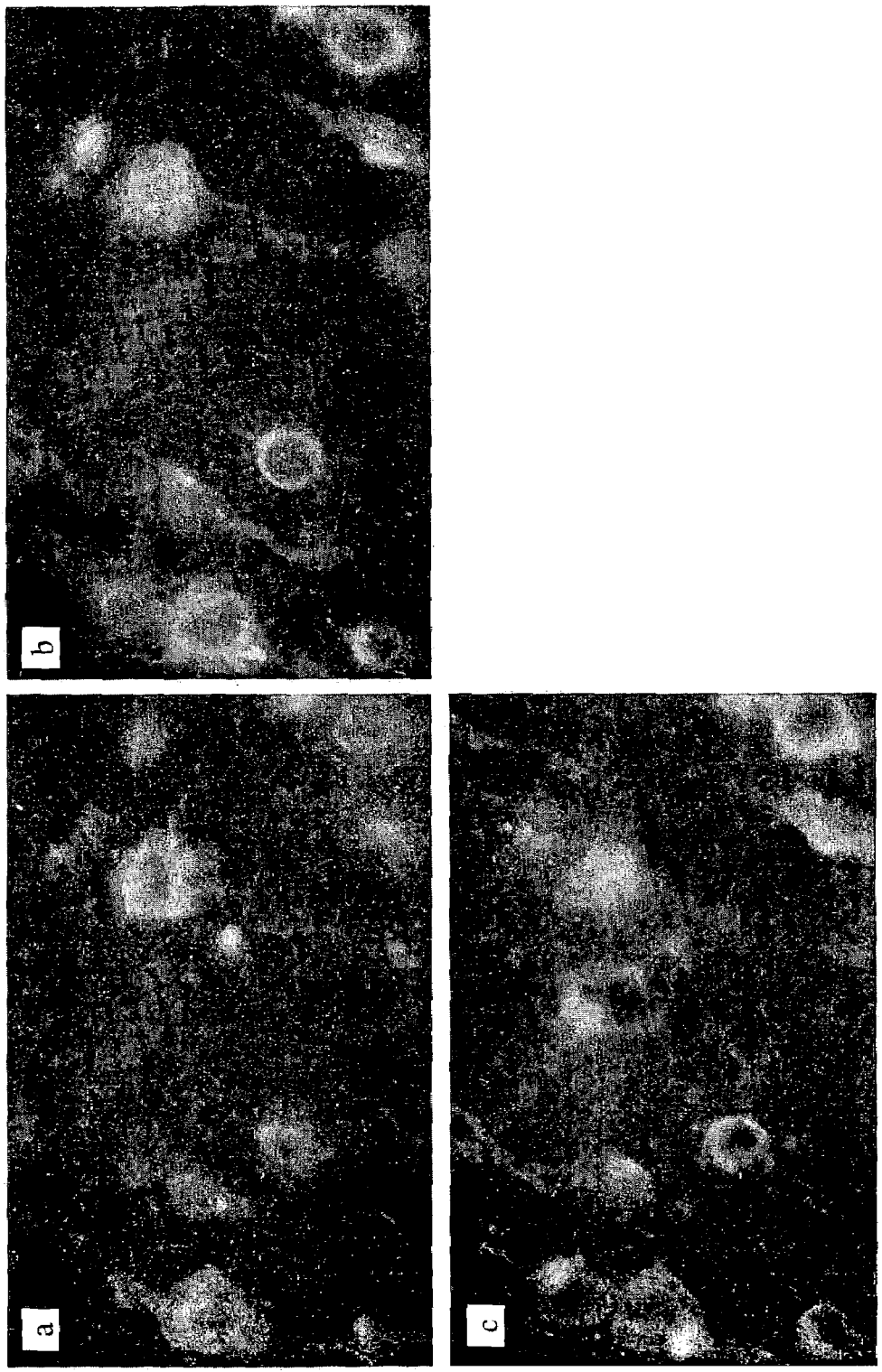
FIG. 4 shows co-localization of bIII-tubulin (a neural marker) and BrdU immunoreactivity in the same cells. (a-c) Three different planes of the same microscopic view. The bIII-tubulin positive cells (green) show BrdU positive nuclei (red) indicating that these cells are derived from transplanted NSCs.

The transplanted NSCs, with BrdU immunopositive nuclei, were stained for human bIII-tubulin and human GFAP. Double immunolabeling with bIII-tubulin and BrdU in three different planes from the same microscopic view clearly showed the co-localization of these two signals in the same cells (FIG. 4). According to the manufacturer's description, the anti-bIII-tubulin antibody may also recognize the host (rat) bIII-tubulin. Despite this, the specific co-localization of the bIII-tubulin and BrdU at different planes indicate that the majority of bIII-tubulin immunopositive cells were indeed transplanted cells of the invention. This may be because bIII-tubulin is mainly expressed in immature neurons, the majority of which are transplanted cells as disclosed herein. The presence of these cell specific antigens indicates that the transplanted cells of the invention successfully differentiated into neurons and astrocytes, respectively.

NSC culture: NSCs were purchased (BioWhittaker, Walkersville, Md.), and alternatively isolated from human tissue, and cultured in a nonsupplemented, serum-free basal medium comprising HAMS-F12 (Gibco, BRL, Burlington, ON); antibiotic-antimycotic mixture (1:100, Gibco); B27 (1:50, Gibco); human recombinant FGF-2 and EGF (20 ng/ml each, R and D Systems Minneapolis, Minn.) and heparin (5 ug/ml, Sigma, St. Louis, Mo.). The cells were incubated at about 37° C. in a 5% $CO_2$ humidified incubation chamber (Fisher, Pittsburgh, Pa.). To facilitate optimal growth conditions, NSC spheroids were sectioned into'quarters every 2 weeks and fed by replacing 50% of the medium every 4-5 days. To inhibit differentiation, the cells can be propagated-on uncoated flask or a flask that has been treated torepel the cells. To induce differentiation, these cells can be replated in the culture dishes (about $1\times10^5$ per dish) in the serum-free basal medium Eagle (BME), which comprises Earle's salt and L-glutamine, and cultured for about 5 days in the absence of FGF-2 and EGF and without the addition of other extrinsic differentiation factors. NSCs cultured in this serum-free medium can spontaneously undergo differentiation into neural cell types.

Example 2

In Vitro Propagation and Differentiation of NSCs

Figure 5:
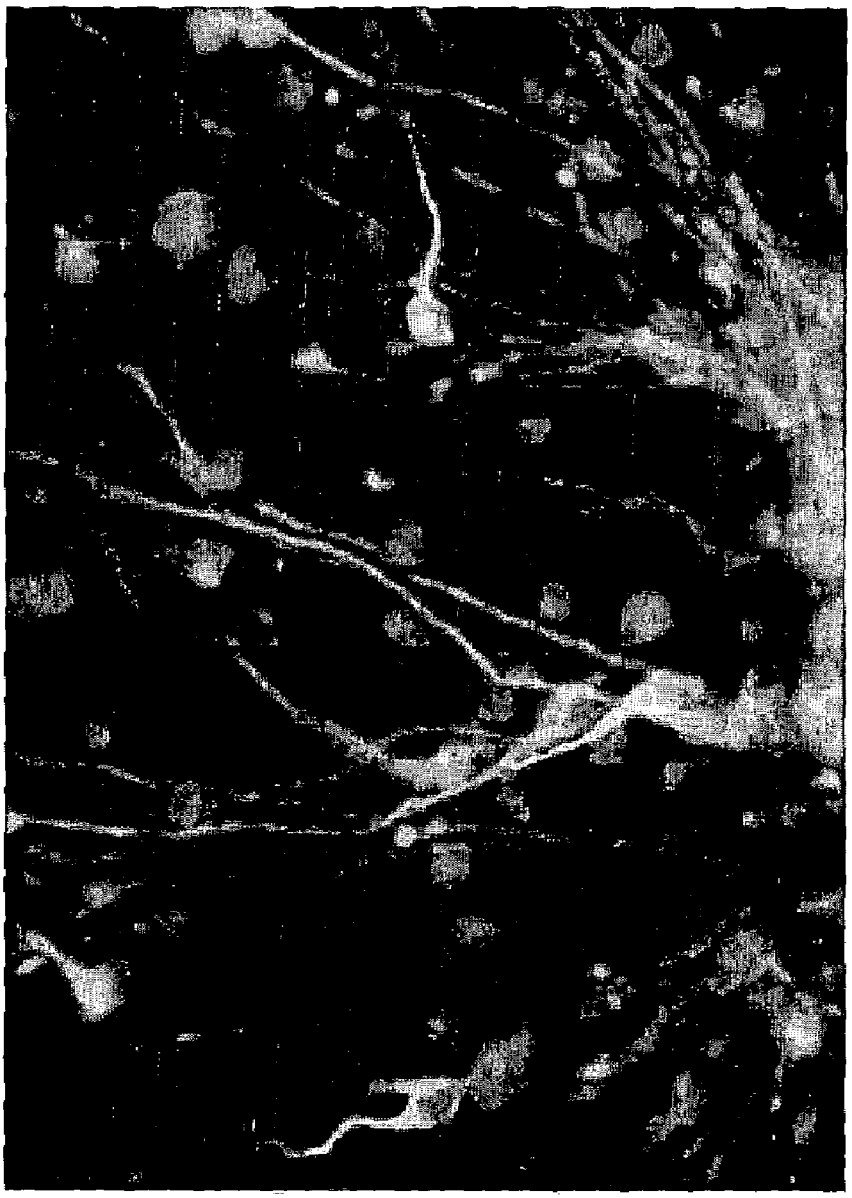
FIG. 5 shows the immunocytochemistry of HNSCs with bIII-tubulin (green, neuron), GFAP (red, astrocytes) and DAPI (blue, nuclei) differentiated in non-serum media.

Neural stem cells have been isolated from embryonic and adult mammalian and human (Doetsch et al., 1999, *Cell* 97: 703-16; Johansson et al., 1999, *Cell* 96: 25-34) centralnervous system (CNS) and propagated in vitro in a variety of culture systems (Svendsen et al., 1999, *Brain Pathol.* 9: 499-513). The inability to grow neural progenitors in culture in the absence of complex and undefined biological fluids (for example, serum) has long been a major obstacle in understanding the physiology of these cells. Long-term culture systems to proliferate NSCs were established (Brannon et al., 2000, *Neuroreport* 11: 1123-8). The ability of multipotent human NSCs to expand in vitro produces well-characterized material for biological research. As grown in ling term culture, NSCs are differentiated into bIII-tubulin- and glial fibrillary acidic protein (GAFP)-immunopositive cells: (Brannon et al., 2000, *Neuroreport* 11: 1123-8). After three years of in vitro expansion, such human NSCs remain capable of producing neurons and glia on differentiation (FIG. 5) under non-serum basal media conditions, indicating the multipotency of these cells, thus demonstrating that this culture system is optimal to maintain NSCs and to investigate their biology.

Figure 6:
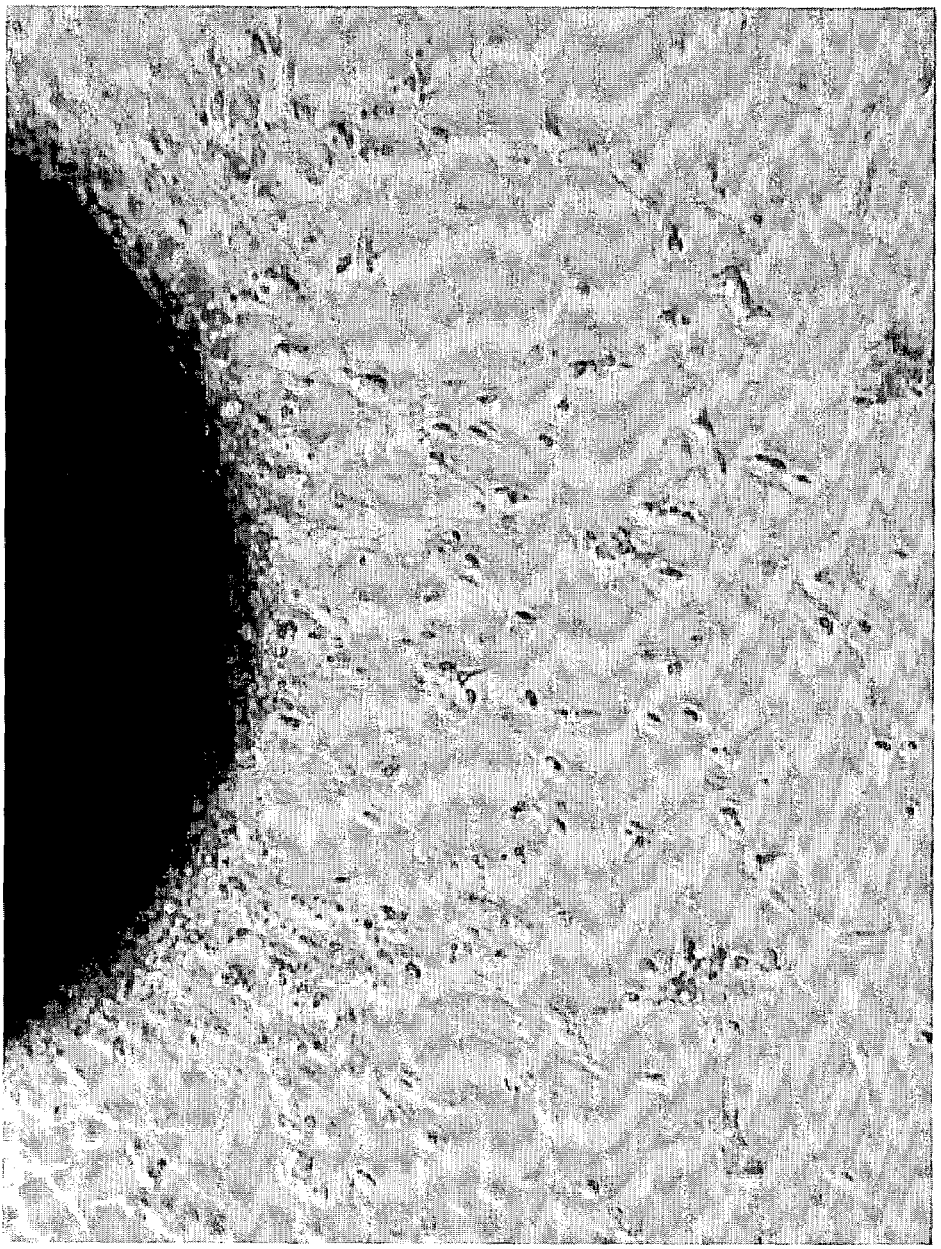
FIG. 6 shows spontaneous differentiation of NSCs in serum-free basal media. Mixed populations of differentiating cells are coronally migrating out from a cluster of cells located on the top of the picture.

Using the growth conditions disclosed herein, clusters of two or more cells can form, from which coronary migrating immature and/or mature neurons and astrocytes can derive (FIG. 6).

Example 3

Retinal Differentiation of NSCs with TGF-b3 Treatment In Vitro

Several studies have found that NSCs migrate into retinal tissue after transplantation into the eye, but none of these investigators has been able to detect opsin expression in these cells (Nishida et al., 2000, Invest Ophthalmol Vis Sci 41: 4268-74; Kurimoto et al., 2001, Neurosci Lett. 306: 57-60;

Warfvinge et al., 2001, Exp. Neurol. 169: p. 1-12), indicating that NSCs do not spontaneously differentiate into photoreceptor cells. This observation was confirmed by immunostaining NSCs differentiated under basal condition without any additional factors, which did not demonstrate opsin expression. Thus, NSC cell fates were modified by epigenetic means using factors known to modify the proliferation or the differentiation of retinal progenitors during development. Previously, opsin-positive cells were produced from NSCs in vitro or in vivo through exposure of TGF-b3.

Figure 7:
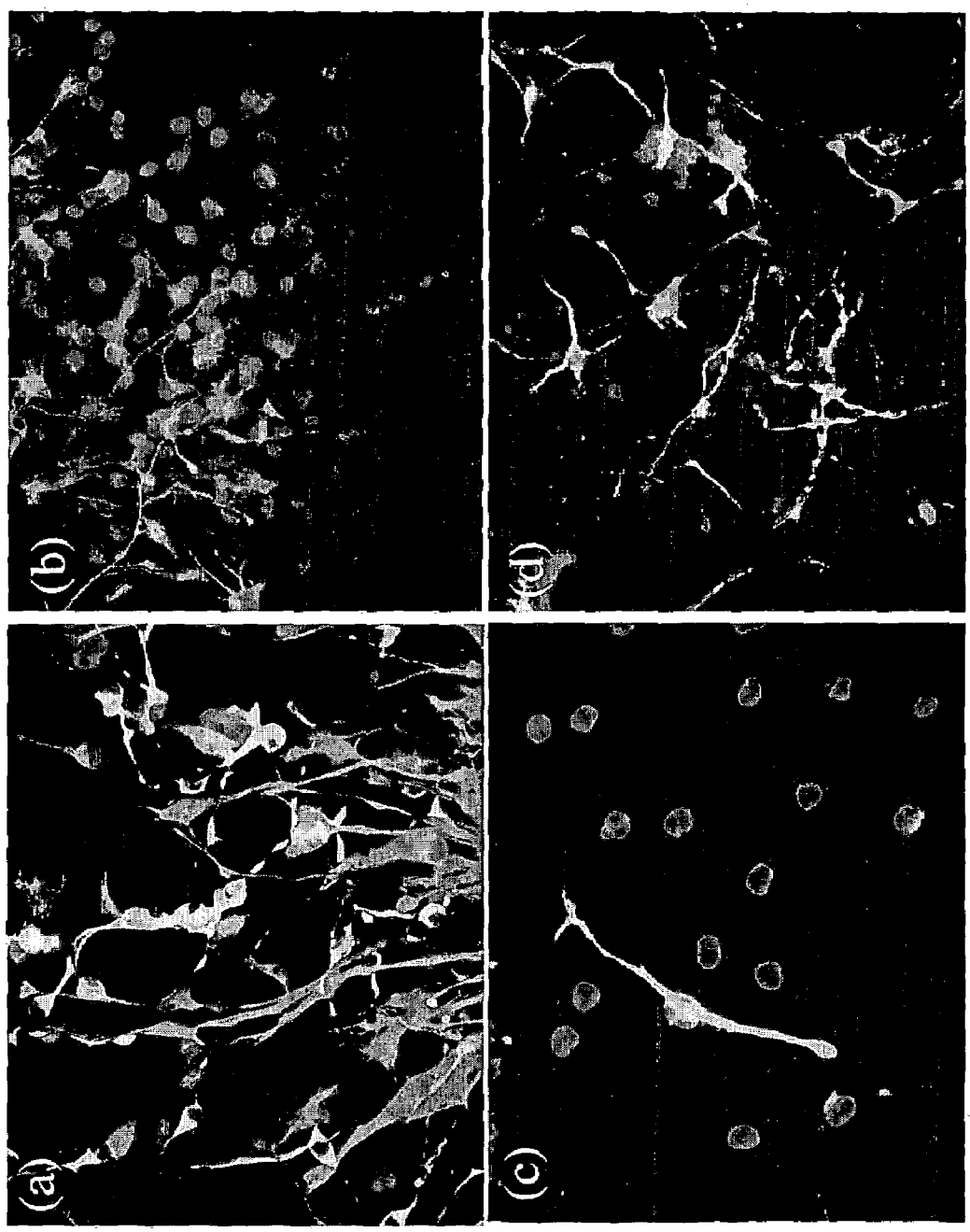
FIGS. 7(I) and (II) shows differentiation of human NSCs into retinal cells in vitro. All nuclei were counter stained by DAPI (blue). (I.a) Typical immunocytochemistry of NSCs differentiated in basal media. Double-immunofluorescence staining was performed using GFAP (red) and bIII-tubulin (green) markers for astrocytes and neural cells, respectively. (I.b) Typical immunocytochemistry of NSCs differentiated in basal media after 5 days differentiation. Cells were double-immunofluorescence stained with GFAP (red) and opsin (green) markers for astrocytes and photoreceptor cells, respectively. Opsin immunoreactivity was not detected in NSCs spontaneously differentiated in basal media condition without any additional factors. (I.c) Typical immunocytochemistry of NSCs differentiated in basal media under the influence of transforming growth factor-beta3 (TGF-b3, 100 ng/ml). Double-immunofluorescence staining with GFAP (red) and opsin (green) markers for astrocytes and retinal cells, respectively. (I.d) Typical immunocytochemistry of NSCs differentiated in basal media in the absence of TGF-b3 after 3 days treatment with 100 ng/ml of TGF-b3. Double-immunofluorescence staining with GFAP (red) and opsin (green) markers for astrocytes and retinal-cells, respectively. The cells of FIG. 7 (II) were grown in serum-free differentiation conditions in the presence of 20 ng/ml of IGF-1 (II.a), 100 ng/ml of TGF-b3 (II.b), 10 ng/ml of CNTF, or without the preceding factors (control; II.d). Double immunofluorescence staining with GFAP (red), opsin (green), markers for astrocytes and retinal cells, respectively. The blue signal represents counter staining for nuclei by DAPI. The NSCs can differentiate into retinal cells through the action of the growth factors in vitro.

Two kinds of differentiation studies were performed: treatment of human NSCs with factors (i) before and (ii) during spontaneous differentiation under a basal media condition. In the first example, NSCs were differentiated under a serum-free differentiation condition in the presence of TGF-b3 (R&D, 50 ng/ml (1 ng/ml to 1 ug/ml)) and VEGF (R&D, 50 ng/ml (1 ng/ml to 1 ug/ml)) for 5 days in Lab-Teck II chamber slides (Nalge Nunc). The second example elucidated whether pretreatment of NSCs is sufficient to produce retinal lineages in these cells. The NSCs were treated with these factors for 3 days, and then differentiated for 5 days under the serum-free differentiation condition in the absence of these factors in the Lab-Teck II chamber slides. As a control, human NSCs were differentiated for 5 days in a no-factor treatment under a serum-free differentiation condition. After differentiation, cells were examined by double-immunofluorescent-cytochemistry (Kim et al., 2002, Proc. Natl. Acad. Sci. USA 99: 4020-5) with antibodies in a combination of goat anti-GFAP (1:100, Research Diagnostics) and mouse anti-B-tubulin (1:700, Sigma) or mouse anti-opsin (1:200, Chemicon). NSCs could be differentiated into opsin-positive cells in vitro by treating these cells with human recombinant TGF-b3 not only before but also during spontaneous differentiation (FIG. 7c,d). No opsin-positive cells were detected in the spontaneous differentiation without TGF-b3 (FIG. 7b), the treated cells were positive for bIII-tubulin and GFAP (FIG. 7a). These results indicated that TGF-b3 treatment is necessary to induce photoreceptor lineage in NSCs. Furthermore, the fact that pretreatment with TGF-b3 was sufficient to transform NSC lineages into retinal cell lineages suggested that transplantation of NSCs into the rodent vitreous cavity could result in differentiation of these cells into retinal tissue. Despite successful differentiation of NSCs treated with TGF-b3 into opsin-positive cells in vitrolin vivo, no opsin-positive cells were detectable by VEGF treatment (data not shown). Thus, TGF-b3 and VEGF treatment were not sufficient to confer retinal cell-differentiation to MeSCs, cells that are less developmentally potent with respect to NSCs (i.e., the MeSCs can readily differentiate into a narrower group of tissue specialized cells), hence requiring the action of BrdU pre-treatment to elicit retinal cell differentiation.

Example 4

Migration and Differentiation NSC of the Invention After Transplant into Rat Vitreous Cavity For transplanting NSCs into the vitreous cavity of rats, cells were cultured with the long-term maintenance media as described above, containing TGF-b3 (1 ng/ml to 10 micrograms/ml; here 100 ng/ml) and about 2 µM 5-bromo-2'-deoxyuridine (BrdU) for 3 days in a 6-well tissue culture without differentiations before injection.

An injury was intentionally made by a needle while these cells were injected to facilitate the migration of NSCs. After an injury, 20 µl of cell suspension, containing about $1.5 \times 10$ to $2 \times 10$ cells, was slowly injected into the intravitreous space of the right eye. The left eye was left intact as a control without injection. At 30 days post-transplantation, the rats were sacrificed and their eyeballs were removed whole. Then these eyeballs were paraffin embedded and sliced into 5 µm sections. The sections were stained with double-immunofluorescent-cytochemistry using rat anti BrdU (1:600, Accurate Chemical & Scientific Corp.) and mouse anti-rhodopsin (1:200, Chemicon), and mounted on slides, then coverslipped using VECTASIELD mounting medium (Vector) with DAPI.

Figure 8:
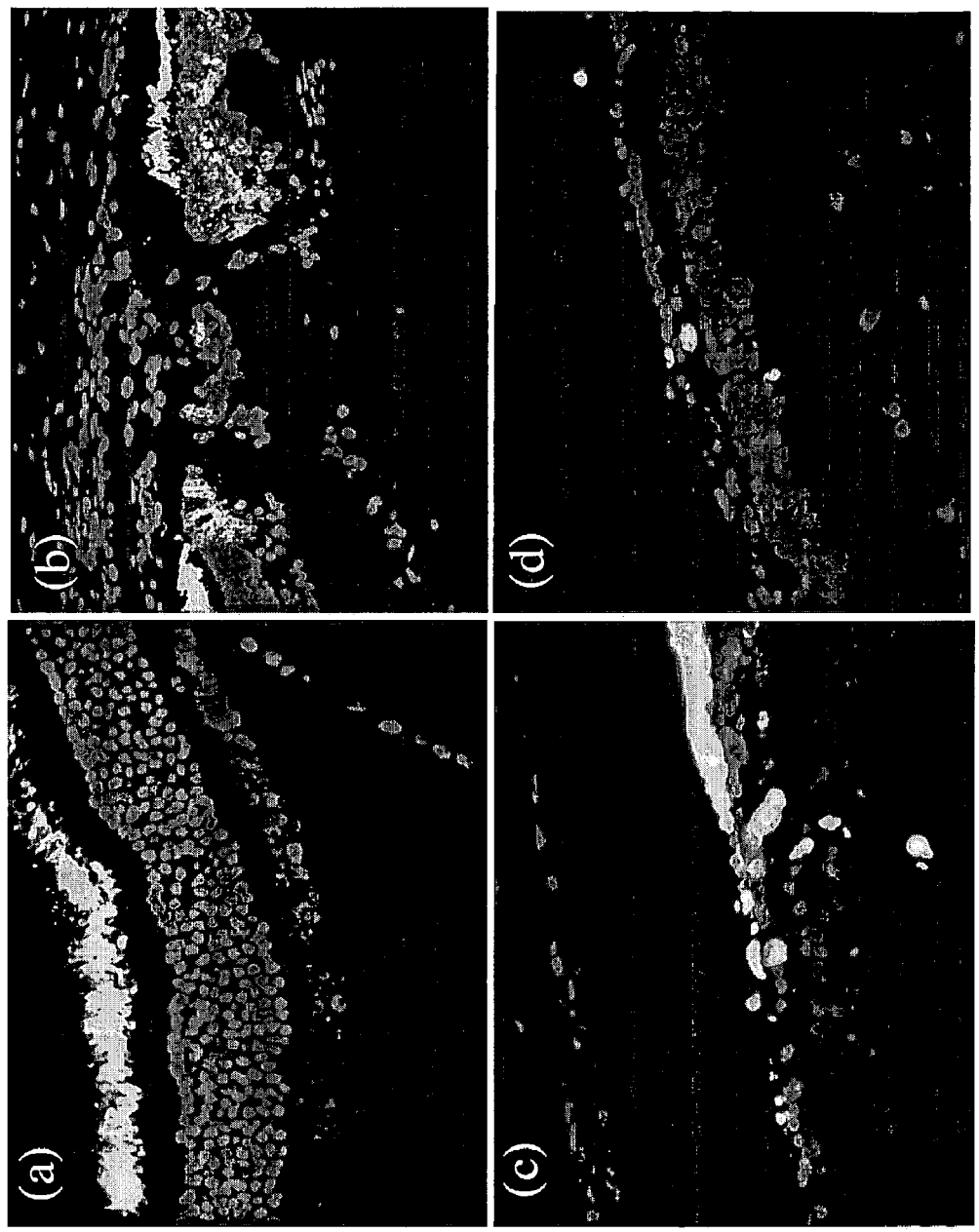
FIGS. 8 (I) and (II) shows differentiation of NSCs into retinal cells in vivo. All nuclei were counterstained by DAPI (blue). (a) Typical immunocytochemistry of a control retinal section without any lesion or NSC transplantation (×100). The section was double-immunofluorescence stained with BrdU (red) and opsin (green) markers for donor cells and photoreceptor cells, respectively. (b) Typical immunocytochemistry of retinal sections 4 weeks after a lesion and NSC transplantation (×100). The section was double-immunofluorescence stained with BrdU(red) and opsin (green) markers for donor cells and photoreceptor cells, respectively. NSCs migrated into damaged area of the retinal tissue. A higher magnification (c, ×400) shows that these migrating NSCs also show cytosolic expression of opsin. (d) Typical in situ hybridization histochemistry for human opsin gene expression using human-specific opsin sequence riboprobes in a section next to the section immunostained in (c). Human opsin gene expression is visualized in green fluorescent stain.

FIG. 8(I) shows the immunocytochemistry and in situ hybridization histochemistry (ISHH) of the hybridization histochemistry (ISHH) of the retinal sections 4 weeks after transplantation of NSCs pretreated with BrdU and TGF-b3. Extensive migration of these cells into the lesioned area of the retina was found (FIG. 8(I)b), similar to other researchers, who found migration and incorporation of neural stem cells into the retina after intraocular (Nishida et al., 2000, Invest Ophthalmol Vis Sci 41: 4268-74; Kurimoto et al., 2001, Neurosci Let. 306: 57-60; Warfvinge et al., 2001, Exp. Neurol. 169: 1-12). However, for the first time is, demonstrated herein that human stem cells incorporated into the photoreceptor layer are in fact able to express opsin immunoreactivity (FIG. 8(I)c), in contrast to previous studies that did not report such findings (ibid). Since anti-opsin antibody that recognized both human and rat opsin protein was used, it was not determined whether opsin is expressed by the donor (human stem cells) or by the host (rat cells). To overcome this technical problem, ISHH was conducted as described below against the human rhodopsin gene-encoding region. The cloned human rhodopsin gene sequence does not recognize any other species of opsin genes listed by Genbank: in particular, this sequence does not show a significant similarity to any DNA sequence found in rat genes (data not shown). Using the human opsin gene sequence as a DIG-labeled RNA probe, human opsin expression was detected in the retina following human stem cells transplantation (FIG. 8(I)d). These results indicate that both NSCs pretreated with BrdU and TGF-b3 not only were incorporated into the rat retina, but they also differentiated into photoreceptor cells. NSCs that were not pre-treated with BrdU, according to the methods of the invention were not able to migrate and differentiate in a tissue-appropriate manner in vivo. FIG. 8(II) shows immunocytochemistry of retinal sections 8 days after transplantation to the eye of NSCs pretreated with TGF-b3, IGF-1 or CNTF. NSCs grown in basal media differentiated to opsin-expressing cells in vivo after exposure to IGF-1, TGF-b3 or CNTF for four days. Cells were treated with 20 ng/ml of IGF-1 (8(II).a), 100 ng/ml of TGF-b3 (8(II).b), or 10 ng/ml of CNTF (8(II).c) prior to transplantation into rat eye. Double immunofluorescence staining with GFAP (red), opsin (green), markers for astrocytes and-retinal cells, respectively. The blue signal represents counter staining for nuclei by DAPI. The transplanted NSCs can differentiate into retinal cells through the action of the growth factors.

Construction of exemplary human-specific opsin riboprobe-vectors: A 360 bp fragment of a human-specific rhodopsin gene sequence (from 6241 bp to 6601 bp of U49742) was selected. The selected human rhodopsin gene sequence does not have a significant level of homology with other rhodopsin genes from other species. In particular, this sequence does not show a significant similarity to any DNA sequence found in the rat genome (data not shown). The selected human-specific rhodopsin gene sequence was amplified from human genome DNA by PCR using a forward primer(5'-TTCCCAATGAGGGTGAGATT-3'; SEQ ID NO: 1) and a reverse primer (5'-GGAATTTCCCACTCTTTGTT-3'; SEQ ID NO: 2). PCR amplification was conducted in 50 µl volumes containing control human genomic DNA (100 ng, Invitrogen), 1×amplification buffer (Invitrogen), 40 nM of each primer, dNTP Mix (250 µM, Invitrogen) and Taq DNA Polymerase (2.5U, Invitrogen), under conditions of: 95° C. (30 seconds), 52° C. (30 seconds), and 72° C. (60 seconds) for 30 cycles. The PCR-amplified fragment was ligated into a TOPO TA cloning in vitro transcription vector (Invitrogen) after gel purification on 2% agar gel. The plasmid was transformed into E. coli-competent cells (Strategene) and the clone was confirmed by sequencing the insert.

In situ hybridization histochemistry for human opsin mRNA in paraffin embedded sections: Digoxigenin-labeled human opsin-specific riboprobes are made by in vitro transcription. Reactions (20 µl) were performed in a reaction mixture containing 4 µl of 5×transcription buffer (USB Corporation), 2 µl of 10×digoxigenin RNA-labeling mix (0.2 µg/ml, Roche), 1 µl of template DNA (PCR reaction described above, 100 ng/µl); 2 µl of T7 RNA polymerase (5U/µl, USB), and 11 µl of molecular biology grade water. After mixing with a pipette, the reaction mixture was incubated at room temperature for 2 hours. The probe was purified by ethanol precipitation and dissolved in 100 µl, molecular biology-grade water. 10 µl of this probe solution was used to make the hybridization mixture. Rat eye sections were deparaffinized with xylene (Fisher) for 5 minutes at room temperature, and rehydrated using a serial concentration of ethanol (Fisher) and distilled water at room temperature. The sections were then washed with 0.1 M phosphate-buffered saline (PBS), pH 7.4, for 15 minutes at room temperature followed by incubation with 10 ng/ml of proteinase K (Sigma) for 30 minutes at 37° C. The sections were washed twice in glycine solution (0.75 g glycine/100 ml of 0.1 M PB, pH 7.4) for 5 minutes at room temperature and treated with 13% triethanolamine solution (pH 8.0) containing 2.5% acetic anhydride for 10 minutes at room temperature. The sections were then prehybridized with hybridization buffer after 2 washes with 2×SSC (saline-sodium citrate buffer, Sigma, pH 7.0) for 15 minutes each at room temperature (RT). Hybridization buffer consists of 50% formamide, 1×Denhardt's solution, 10% dextran sulfate (Invitrogen), 4×SSC, 0.25 mg/ml yeast tRNA, and 0.3 mg/ml herring sperm DNA. Hybridization was done in the hybridization buffer containing 10 µl of digoxygenin riboprobe as described above for 18 hours at 60° C. After hybridization, the sections were washed twice with 4×SSC buffer, followed by a stringency wash with 50% formamide and 2×SSC for 30 minutes at 60° C. The sections were washed twice with RNase buffer (10 mM Tris, pH 8.0, 0.5 M NaCl, 1 mM EDTA) for 10 minutes at room temperature and then incubated with RNase solution (50 ug/ml of RNase (Promega) in RNase buffer) for 30 minutes at 37° C. The sections were washed with serial concentration of SSC buffer (2×, 0.5×, 0.1×) twice for 20 minutes at 60° C., except that the last wash was done at RT. After rinsing with PBS, the probe was visualized by immunodetection of digoxygenin with a primary antibody, sheep anti-digoxigenin (1:500, Roche), and secondary antibody with fluorescein (FITC)-conjugated AffiniPure donkey anti-sheep IgG (1:200, Jackson Laboratories).

Image and data analysis: Digitally-captured images from fluorescent microscopy of cultured cells can be analyzed by NIH Image software (NIH) with Cell Scoring, Particle Analysis, and Cell Analysis macros. The number of cells showing particular antibody markers in the areas of interest can be counted. In addition, total, cell number can be counted by DAPI nuclei counterstaining and each cell population will be expressed as a percentage of the total cell number. The results from each treatment condition can be analyzed by ANOVA and followed by post-hoc (Fisher's Protected LCD) analysis.

Example 5

Transplantation of MNSCs of the Invention to Nucleus Basalis Magnocellularis (NBM) Lesion Rat Model Stem cell transplantation strategies are advocated in Alzheimer's disease (AD) neuroregeneration therapy: Basal cholinergic neurons, which are selectively degenerated in AD, extend long projections into the cortex and hippocampus. An open question for neuroreplacement treatment for AD is whether these degenerating cholinergic cells can be replaced by the transplantation of stem cells. To answer this question, cells of the invention were transplanted into nucleus basalis magnocellularis (NBM) lesion model rats. The lesions were induced either by an injection of ibotenic acid or by anti-NGF receptor antibody conjugated with saporin (Advanced Targeting System, San Diego, Calif.). Cells prepared according to the invention were simultaneously injected into the contralateral side of the lateral ventricle (Qu, 2001) of the NBM-lesioned animal. Four weeks after the surgery, the brain was examined by immunohistochemistry. Many GFAP-positive cells were detected in the lesioned area, but they were not BrdU-positive, indicating astrocytes activation in this area. BrdU-positive cells with ChAT or bIII-tubulin immunoreactivity were found in the lesion site, indicating that MNSCs of the invention migrated from the contralateral ventricle to the lesion site and had differentiated into cholinergic and other neural cells. These neurally differentiating cells were neurons that appeared rather morphologically premature. Our results indicate a positive study of neuroreplacement treatment for cholinergic neurons in, AD.

Transplantation of cells of the invention: Male SD rats were deeply anesthetized with sodium pentobarbital (50 mg/kg, i.p.). Using bregma as a reference point, about $1 \times 10^5$ cells of the invention were collected and slowly injected into the right lateral ventricle (AP 1.4; ML 3.3; and DV 4.5 mm) of the rat brain using a stereotaxic apparatus (Devid Kopff).

Cholinergic lesions induced by 192-IgG-saporin conjugate: Male Sprague-Dawley rats, 4-months-old, are anesthetized with 50 mg/kg pentobarbital and mounted in a stereotaxic apparatus (David Kopf). Unilateral NBM injections of the 1 µg/2 µl 192-IgG-saporin conjugate toxin (in a vehicle of sterile filtered 200 mM phosphate buffer (pH 7.4)) were performed using a microsyringe. The NBM was stereotaxically localized using the following coordinates: AP=−2.3 mm from bregma, ML=±3.7 mm, 7.5 mm below dura. The toxin was delivered over 5 minutes and the needle was left in place for another 5 minutes following injection.

Immunohistochemistry: The rats were sacrificed by an overdose of anesthesia (sodium pentobarbital, 70 mg/kg, i.p.) and perfused with phosphate buffered saline (PBS) followed by 4% paraformaldehyde. Brains were removed and placed into the 4% paraformaldehyde fixative containing 20% sucrose for overnight. The brains were sliced into 20 µm, coronal sections using cryomicrotome. The sections were washed briefly in PBS and pretreated with 1M HCL for 30 minutes at room temperature (RT) and neutralized with sodium borate (0.1M, pH 8.0) for 30 minutes, in order to increase the accessibility of the anti-BrdU antibody to the BrdU incorporated in the cell nuclei. After rinsing with PBS, sections were transferred to a solution containing 0.25% Triton X-100 in PBS (PBST) for 30 minutes. Then the sections were blocked in PBST containing 3% donkey normal serum for 1 hr and incubated in mouse anti-BrdU (1:200; DSHB, Iowa City, Iowa) or sheep anti-BrdU (1:1000; Jackson IR Laboratories, Inc. West Grove, Pa.) diluted in PBST overnight at 4 degC. The sections were then washed with PBS and incubated with mouse IgG2b monoclonal anti-human bIII-tubulin, clone SDL3D10 (1:500, Sigma), rat IgG monoclonal anti-ChAT (1:500, Boerhinger-Mannheim) and goat anti-human-glial filament protein, N-terminal human affinity purified (1:200, Research Diagnostics Inc., Flander, N.J.), respectively, for overnight at 4 degC in the dark. After rinsing in PBS, donkey anti-mouse, donkey anti-rat, donkey anti-goat or donkey anti-sheep IgG conjugated, with rhodamine or FITC (Jackson IR Laboratories, Inc.) are added at 1:200 dilution in PBST for 2 hours at RT in the dark. Sections were then washed with PBS thoroughly before mounting on glass glides. The sections were coverslipped with mounting media containing DAPI for nucleus counter staining.

Figure 9:
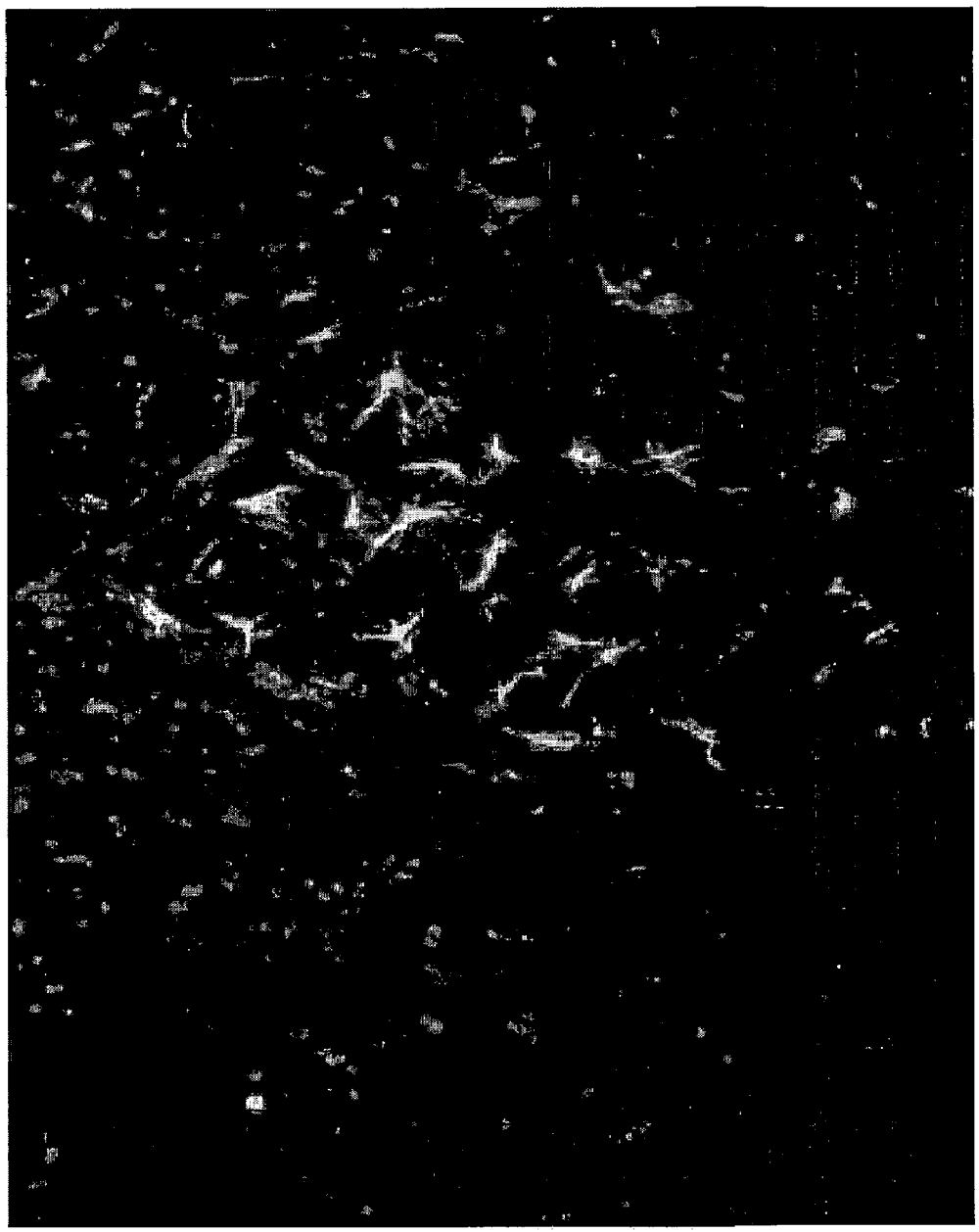
FIG. 9 shows increased GFAP imrmunoreactivity in the NBM 4 weeks after saporin lesion. Green: GFAP; Blue: DAPI.
Figure 10:
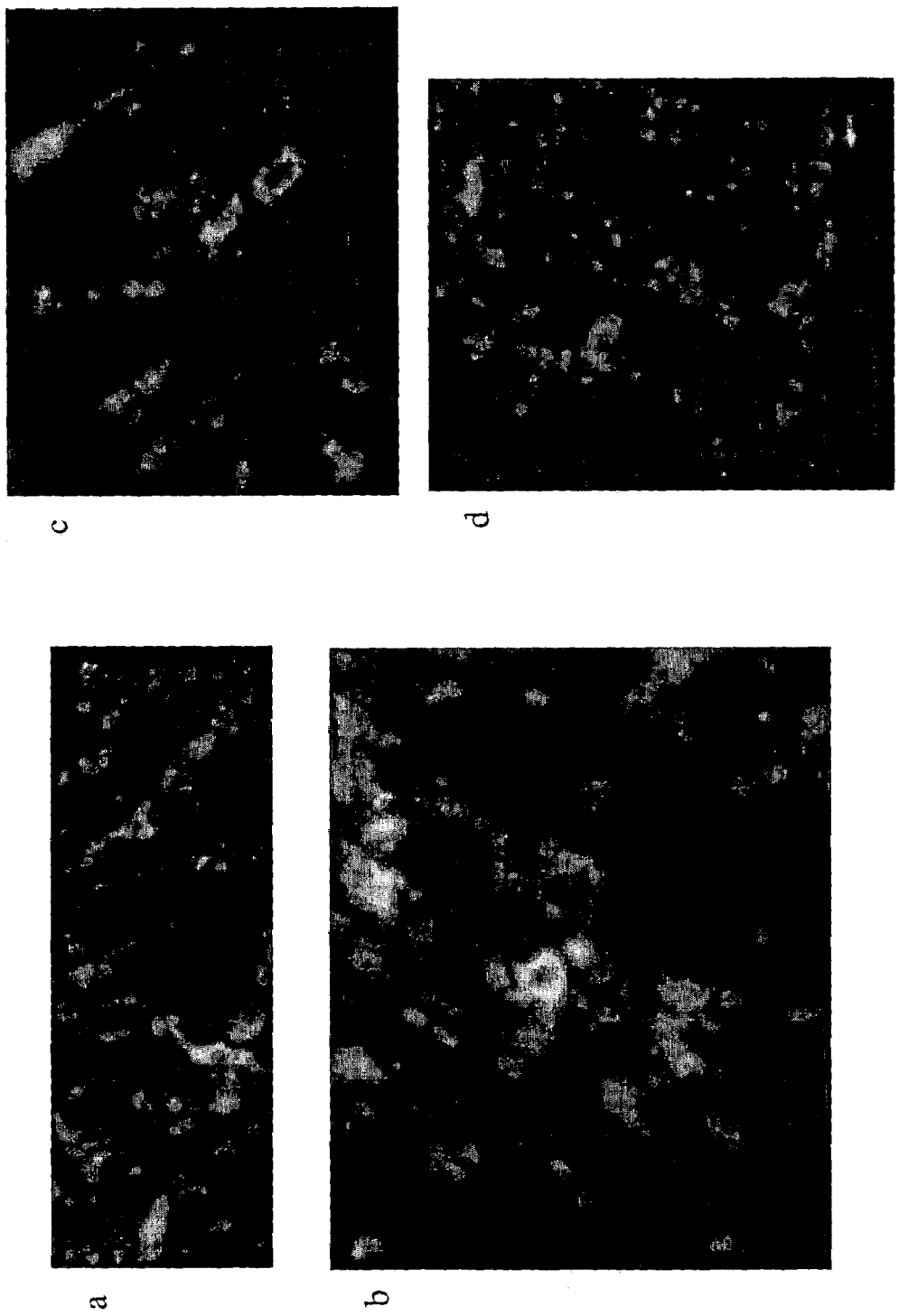
FIG. 10 shows choline acetyltransferase (ChAT) immunoreactivity in BrdU positive cells in the lesion site indicating replacement of lesioned cells by the transplanted cells of the invention (a-c; Green: ChAT; Red: BrdU; Blue: DAPI) and ChAT immunoreactivity in human nuclei positive cells in the lesion site (d; Green: CHAT; Red: human nuclei; Blue: DAPI).
Figure 11:
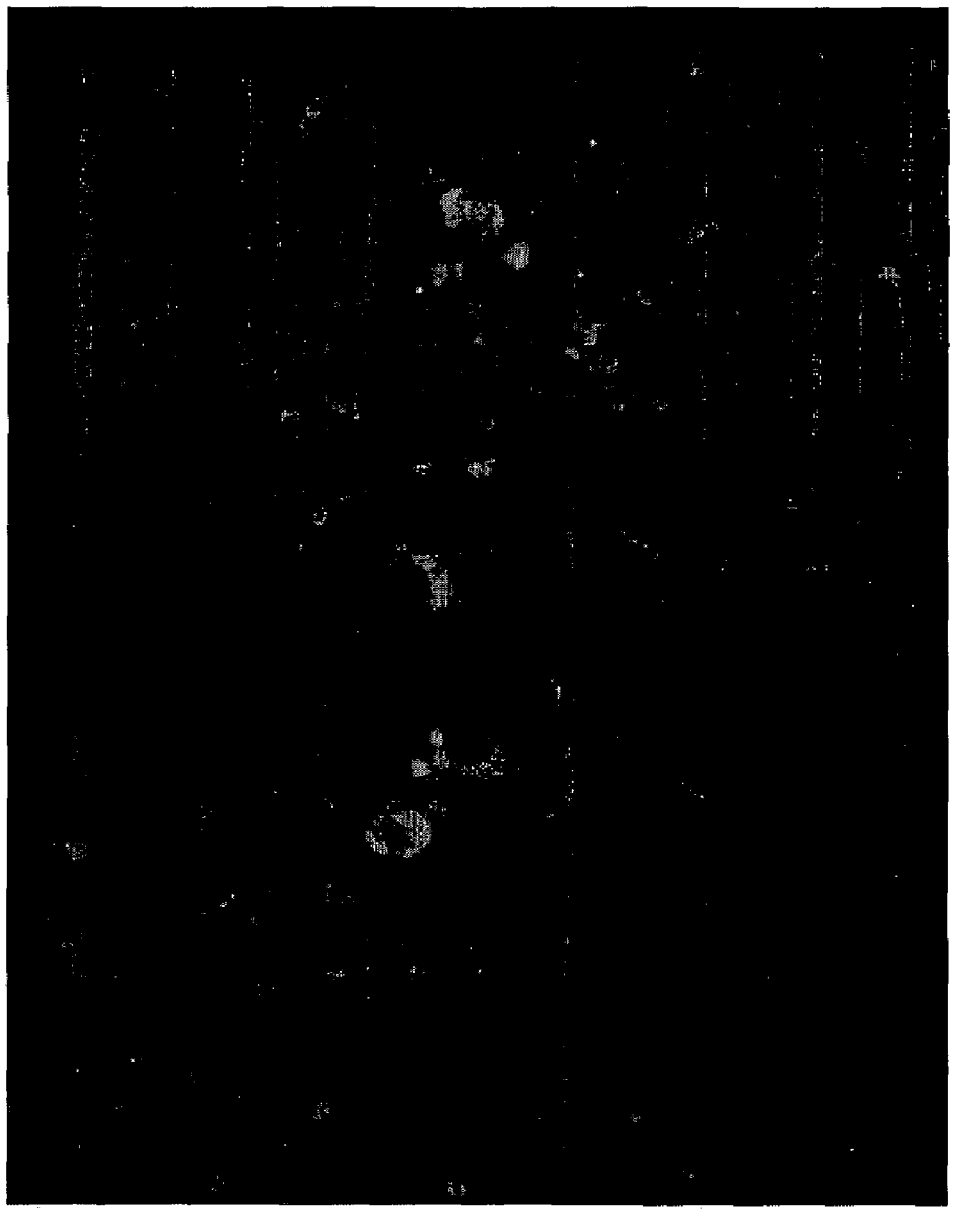
FIG. 11 shows human nuclei immunoreactivity-positive cells that were observed in the lesion area. Red: human nuclei; Blue: DAPI.
Figure 12:
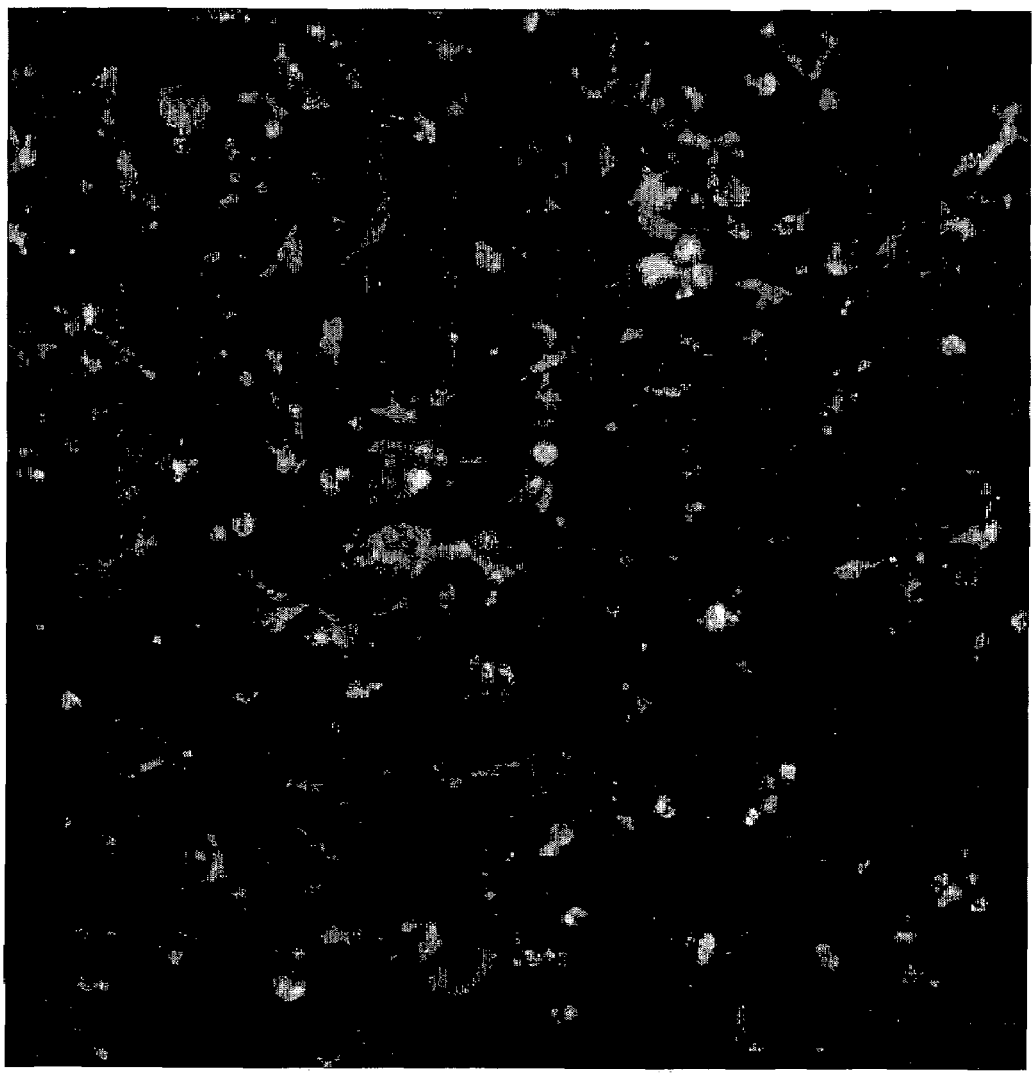
FIG. 12 shows GFAP and human nuclei immunoreactivity in the lesion site. Green: GFAP; Red: human nuclei; Blue: DAPI.

Increased GFAP immunoreactivity in the NBM was observed 4 weeks after saporin lesion. (FIG. 9. Green: GFAP; Blue: DAPI). Choline acetyltransferase (ChAT) immunoreactivity was also observed in BrdU positive cells in the lesion site (FIG. 10a-c. Green: ChAT; Red: BrdU; Blue: DAPI), indicating replacement of lesioned cells by the transplanted cells of the invention. Further, ChAT immunoreactivity was observed n human nuclei positive cells in the lesion site. (FIG. 10d. Green: ChAT; Red: human nuclei; Blue: DAPI). Human nuclei immunoreactivity-positive cells were observed in the lesion area (FIG. 11. Red: human nuclei; Blue: DAPI) and GFAP and human nuclei immunoreactivity were observed in the lesion site. (FIG. 12. Green: GFAP; Red: human nuclei; Blue: DAPI). A large number of transplanted cells migrated to the lesion site and differentiated into rather mature neurons and glia 4 weeks after transplantation. The lesion appears to attract the cells of the invention, indicating a possible release of the migration factor(s) from the lesion site.

It should be understood that the foregoing disclosure emphasizes certain specific embodiments of the invention and that all modifications or alternatives equivalent thereto are within the spirit and scope of the invention as set forth in the appended claims.

We claim:

1. One or a plurality of mammalian multipotent neural stem cells that can form a cluster produced according to the method comprising the steps of:
    a. isolating mammalian neural stem cells from mammalian neural tissue containing at least one neural stem cell,
    b. culturing the neural stem cells in a cell culture media under conditions that permit proliferation of the neural stem cells in vitro, in the presence of substituted deoxynucleotide or deoxynucleoside in an amount effective to adapt the cells to proliferate, migrate and differentiate when transplanted into host tissue and at least one growth factor, wherein cells are cultured in an uncoated flask or a flask that has been treated to repel the cells, and wherein the substituted deoxynucleotide or deoxynucleoside is bromodeoxyuridine, bromodeoxycytidine, bromodeoxyguanosine, methyldeoxythymidine, or chlorodeoxyuridine, to generate the one or a plurality of mammalian multipotent neural stem cells that can form a cluster, and
    c. thereafter harvesting the one or plurality of mammalian multipotent neural stem cells that can form a cluster produced in (b).

2. A composition comprising, as an active ingredient, the one or
    a plurality of mammalian multipotent neural stem cells that can form a cluster produced according to the method comprising the steps of:
    a. isolating mammalian neural stem cells from mammalian neural tissue containing at least one neural stem cell,
    b. culturing the neural stem cells in a cell culture media under conditions that permit proliferation of the neural stem cells in vitro, in the presence of substituted deoxy-

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: Forward primer
<220> FEATURE:
<221> NAME/KEY: misc_feature
<222> LOCATION: (1)..(20)
<223> OTHER INFORMATION: Forward primer

<400> SEQUENCE: 1
ttcccaatga gggtgagatt                                              20

<210> SEQ ID NO 2
<211> LENGTH: 20
<212> TYPE: DNA
<213> ORGANISM: Artificial
<220> FEATURE:
<223> OTHER INFORMATION: Reverse primer
<220> FEATURE:
<221> NAME/KEY: misc_feature
<222> LOCATION: (1)..(20)
<223> OTHER INFORMATION: Reverse primer

<400> SEQUENCE: 2
ggaatttccc actctttgtt                                              20
``` nucleotide or deoxynucleoside in an amount effective to adapt the cells to proliferate, migrate and differentiate when transplanted into host tissue and at least one growth factor, wherein cells are cultured in an uncoated flask or a flask that has been treated to repel the cells, and wherein the substituted deoxynucleotide or deoxynucleoside is bromodeoxyuridine, bromodeoxycytidine, bromodeoxyguanosine, methyldeoxythymidine, or chlorodeoxyuridine, to generate the one or a plurality of mammalian multipotent neural stem cells that can form a cluster, and c. thereafter harvesting the one or plurality of mammalian multipotent neural stem cells that can form a cluster produced in (b).

3. A pharmaceutical composition comprising, as an active ingredient, one or a plurality of mammalian multipotent neural stem cells that can form a cluster produced according to the method comprising the steps of:

a. isolating mammalian neural stem cells from mammalian neural tissue containing at least one neural stem cell, b. culturing the neural stem cells in a cell culture media under conditions that permit proliferation of the neural stem cells in vitro, in the presence of substituted deoxynucleotide or deoxynucleoside in an amount effective to adapt the cells to proliferate, migrate and differentiate when transplanted into host tissue and at least one growth factor, wherein cells are cultured in an uncoated flask or a flask that has been treated to repel the cells, and wherein the substituted deoxynucleotide or deoxynucleoside is bromodeoxyuridine, bromodeoxycytidine, bromodeoxyguanosine, methyldeoxythymidine, or chlorodeoxyuridine, to generate the one or a plurality of mammalian multipotent neural stem cells that can form a cluster, and c. thereafter harvesting the one or plurality of mammalian multipotent neural stem cells that can form a cluster produced in (b).

4. The pharmaceutical composition according to claim 3 further comprising a pharmaceutically acceptable carrier.

5. A method of preparing one or a plurality of mammalian multipotent neural stem cells that can form a cluster comprising the steps of:

a. isolating mammalian neural stem cells from mammalian neural tissue containing at least one neural stem cell, b. culturing the neural stem cells in a cell culture media under conditions that permit proliferation of the neural stem cells in vitro, in the presence of substituted deoxynucleotide or deoxynucleoside in an amount effective to adapt the cells to proliferate, migrate and differentiate when transplanted into host tissue and at least one growth factor, wherein cells are cultured in an uncoated flask or a flask that has been treated to repel the cells, and wherein the substituted deoxynucleotide or deoxynucleoside is bromodeoxyuridine, bromodeoxycytidine, bromdeoxyguanosine, methyldeoxythymidine, or chlorodeoxyuridine, to generate the one or a plurality of mammalian multipotent neural stem cells that can form a cluster, and c. thereafter harvesting the one or plurality of mammalian multipotent neural stem cells that can form a cluster produced in (b).

6. The method of claim 5 wherein the growth factor in the culture media prepared in (b) is fibroblast growth factor, epidermal growth factor or combinations thereof.

7. The method of claim 6 wherein the growth factor is fibroblast growth factor or epidermal growth factor.

8. The method of claim 6 wherein the growth factor is fibroblast growth factor.

9. The method of claim 6 wherein the growth factor is epidermal growth factor.

10. The method of claim 5 wherein the culture media of step (b) further comprises heparin.

11. The method of claim 5 wherein said mammalian neural tissue is obtained from an embryo, fetus, infant, juvenile, or adult.

12. The method of claim 5 wherein said mammalian neural tissue is obtained from a human.

* * * * *